(12) United States Patent
Kiesel et al.

(10) Patent No.: US 7,936,463 B2
(45) Date of Patent: *May 3, 2011

(54) CONTAINING ANALYTE IN OPTICAL CAVITY STRUCTURES

(75) Inventors: Peter Kiesel, Palo Alto, CA (US); Oliver Schmidt, Palo Alto, CA (US); Michael Bassler, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/702,325

(22) Filed: Feb. 5, 2007

(65) Prior Publication Data

US 2008/0186494 A1 Aug. 7, 2008

(51) Int. Cl.
*G01B 9/02* (2006.01)

(52) U.S. Cl. ......................... 356/519; 356/454

(58) Field of Classification Search ................... 356/454, 356/480, 519
See application file for complete search history.

(56) References Cited

U.S. PATENT DOCUMENTS

| | | | |
|---|---|---|---|
| 3,915,573 A | 10/1975 | Knoll et al. | |
| 4,427,296 A | 1/1984 | Demarest et al. | |
| 4,455,089 A | 6/1984 | Yeung et al. | |
| 4,573,796 A | 3/1986 | Martin et al. | |
| 4,820,042 A | 4/1989 | Barger | |
| 5,144,498 A | 9/1992 | Vincent | |
| 5,151,585 A | 9/1992 | Siebert | |
| 5,166,755 A | 11/1992 | Gat | |
| 5,243,614 A | 9/1993 | Wakata et al. | |
| 5,312,535 A | 5/1994 | Waska et al. | |
| 5,370,842 A | 12/1994 | Miyazaki et al. | |
| 5,394,244 A * | 2/1995 | Tsai | 356/517 |
| 5,414,508 A | 5/1995 | Takahashi et al. | |
| 5,437,840 A | 8/1995 | King et al. | |
| 5,461,477 A | 10/1995 | Marinelli et al. | |
| 5,572,328 A | 11/1996 | Fouckhardt et al. | |

(Continued)

FOREIGN PATENT DOCUMENTS

DE 19540456 5/1997

(Continued)

OTHER PUBLICATIONS

Liang, X.J., Liu, A.Q., Zhang, X.M., Yap, P.H., Ayi, T.C., Yoon, H.S., "Refractive Index Measurement of Single Living Cell Using a Biophotonic Chip for Cancer Diagnosis Applications," 9th International Conference on Miniaturized Systems for Chemistry and Life Sciences, Oct. 9-13, 2005, 3 pages.

(Continued)

*Primary Examiner* — Hwa S. A Lee
(74) *Attorney, Agent, or Firm* — Hollingsworth & Funk, LLC

(57) ABSTRACT

A device can include both a photosensing component and an optical cavity structure, with the optical cavity structure including a part that can operate as an optical cavity in response to input light, providing laterally varying output light. For example, the optical cavity can be a graded linearly varying filter (LVF) or other inhomogeneous optical cavity, and the photosensing component can have a photosensitive surface that receives its output light without it passing through another optical component, thus avoiding loss of information. The optical cavity part can include a region that can contain analyte. Presence of the analyte affects the optical cavity part's output light, and the photosensing component can respond to the output light, providing sensing results indicating the analyte's optical characteristics.

26 Claims, 14 Drawing Sheets

U.S. PATENT DOCUMENTS

| | | | |
|---|---|---|---|
| 5,666,195 A | 9/1997 | Shultz et al. | |
| 5,682,038 A | 10/1997 | Hoffman | |
| 5,760,900 A | 6/1998 | Ito et al. | |
| 5,784,507 A | 7/1998 | Holm-Kennedy et al. | |
| 5,793,485 A | 8/1998 | Gourley | |
| 5,880,474 A | 3/1999 | Norton et al. | |
| 5,945,676 A | 8/1999 | Khalil et al. | |
| 5,982,478 A | 11/1999 | Ainsworth et al. | |
| 5,982,534 A | 11/1999 | Pinkel et al. | |
| 6,040,578 A | 3/2000 | Malin et al. | |
| 6,049,727 A | 4/2000 | Crothall | |
| 6,091,502 A | 7/2000 | Weigl et al. | |
| 6,108,463 A | 8/2000 | Herron et al. | |
| 6,122,536 A | 9/2000 | Sun et al. | |
| 6,169,604 B1 | 1/2001 | Cao | |
| 6,187,592 B1 | 2/2001 | Gourley | |
| 6,192,168 B1 | 2/2001 | Feldstein et al. | |
| 6,216,022 B1 | 4/2001 | Tyrrell et al. | |
| 6,285,504 B1 | 9/2001 | Diemeer | |
| 6,295,130 B1 | 9/2001 | Sun et al. | |
| 6,310,690 B1 | 10/2001 | Cao et al. | |
| 6,429,022 B1 | 8/2002 | Kunz et al. | |
| 6,438,397 B1 | 8/2002 | Bosquet et al. | |
| 6,459,080 B1 | 10/2002 | Yin et al. | |
| 6,483,959 B1 | 11/2002 | Singh et al. | |
| 6,490,034 B1 | 12/2002 | Woias et al. | |
| 6,519,074 B2 | 2/2003 | Little et al. | |
| 6,529,659 B2 | 3/2003 | Little et al. | |
| 6,561,978 B1 | 5/2003 | Conn et al. | |
| 6,580,507 B2 | 6/2003 | Fry et al. | |
| 6,594,022 B1 | 7/2003 | Watterson et al. | |
| 6,597,461 B1 | 7/2003 | Verma et al. | |
| 6,639,679 B2 | 10/2003 | Frojdh | |
| 6,665,109 B2 | 12/2003 | Little et al. | |
| 6,694,158 B2 | 2/2004 | Polak | |
| 6,697,542 B2 | 2/2004 | Platzman et al. | |
| 6,717,965 B2 | 4/2004 | Hopkins, II et al. | |
| 6,747,775 B2 | 6/2004 | Little | |
| 6,768,555 B2 | 7/2004 | Chen et al. | |
| 6,785,002 B2 | 8/2004 | Zarrabian et al. | |
| 6,795,190 B1 | 9/2004 | Paul et al. | |
| 6,809,865 B2 | 10/2004 | Chen | |
| 6,822,798 B2 | 11/2004 | Wu et al. | |
| 6,839,140 B1 | 1/2005 | O'Keefe et al. | |
| 6,865,198 B2 | 3/2005 | Taubman | |
| 6,867,868 B1 | 3/2005 | Barbarossa | |
| 6,887,713 B2 | 5/2005 | Nelson et al. | |
| 6,906,792 B2 | 6/2005 | Ortyn et al. | |
| 6,934,435 B2 | 8/2005 | Kane | |
| 6,952,603 B2 | 10/2005 | Gerber et al. | |
| 6,983,176 B2 | 1/2006 | Gardner et al. | |
| 7,011,630 B2 | 3/2006 | Desai et al. | |
| 7,012,696 B2 | 3/2006 | Orr et al. | |
| 7,024,236 B2 | 4/2006 | Ford et al. | |
| 7,046,357 B2 | 5/2006 | Weinberger et al. | |
| 7,064,836 B2 | 6/2006 | Bechtel et al. | |
| 7,130,321 B2 | 10/2006 | Spinelli et al. | |
| 7,149,396 B2 | 12/2006 | Schmidt et al. | |
| 7,248,361 B2 | 7/2007 | Kiesel et al. | |
| 7,259,856 B2 | 8/2007 | Kachanov et al. | |
| 7,268,868 B2 | 9/2007 | Kiesel et al. | |
| 7,277,569 B2 | 10/2007 | Bruce et al. | |
| 7,291,824 B2 | 11/2007 | Kiesel et al. | |
| 7,305,112 B2 | 12/2007 | Curry et al. | |
| 7,310,153 B2 | 12/2007 | Kiesel et al. | |
| 7,315,667 B2 | 1/2008 | Schmidt et al. | |
| 7,358,476 B2 | 4/2008 | Kiesel et al. | |
| 7,386,199 B2 | 6/2008 | Schmidt et al. | |
| 7,387,892 B2 | 6/2008 | Kiesel et al. | |
| 7,391,517 B2 | 6/2008 | Trebbia et al. | |
| 7,420,677 B2 | 9/2008 | Schmidt et al. | |
| 7,433,552 B2 | 10/2008 | Kiesel et al. | |
| 7,440,101 B2 | 10/2008 | Auer et al. | |
| 7,466,409 B2 | 12/2008 | Scherer et al. | |
| 7,471,399 B2 | 12/2008 | Kiesel et al. | |
| 7,479,625 B2 | 1/2009 | Kiesel et al. | |
| 7,502,123 B2 | 3/2009 | Kiesel et al. | |
| 7,522,786 B2 | 4/2009 | Kiesel et al. | |
| 7,545,513 B2 | 6/2009 | Kiesel et al. | |
| 7,547,904 B2 | 6/2009 | Schmidt et al. | |
| 7,554,673 B2 | 6/2009 | Kiesel et al. | |
| 7,633,629 B2 | 12/2009 | Kiesel et al. | |
| 2003/0000835 A1 | 1/2003 | Witt et al. | |
| 2003/0020915 A1 | 1/2003 | Schueller et al. | |
| 2003/0137672 A1 | 7/2003 | Moriya et al. | |
| 2003/0161024 A1 | 8/2003 | Zhang et al. | |
| 2003/0179383 A1 | 9/2003 | Chen et al. | |
| 2003/0189711 A1* | 10/2003 | Orr et al. | 356/484 |
| 2003/0191377 A1 | 10/2003 | Robinson et al. | |
| 2003/0235924 A1 | 12/2003 | Adams et al. | |
| 2004/0031684 A1 | 2/2004 | Witt | |
| 2004/0032584 A1 | 2/2004 | Honda et al. | |
| 2004/0038386 A1 | 2/2004 | Zesch et al. | |
| 2004/0067167 A1 | 4/2004 | Zhang et al. | |
| 2004/0132214 A1 | 7/2004 | Lin et al. | |
| 2004/0175734 A1 | 9/2004 | Stahler et al. | |
| 2004/0223135 A1 | 11/2004 | Ortyn et al. | |
| 2004/0223881 A1 | 11/2004 | Cunningham et al. | |
| 2004/0228375 A1 | 11/2004 | Ghosh et al. | |
| 2004/0248318 A1 | 12/2004 | Weinberger et al. | |
| 2005/0042615 A1 | 2/2005 | Smith et al. | |
| 2005/0068526 A1 | 3/2005 | Avrutsky | |
| 2005/0084203 A1 | 4/2005 | Kane | |
| 2005/0099624 A1 | 5/2005 | Staehr et al. | |
| 2005/0124873 A1 | 6/2005 | Shults et al. | |
| 2005/0128479 A1 | 6/2005 | Gilbert et al. | |
| 2005/0158868 A1 | 7/2005 | Trebbia et al. | |
| 2005/0162648 A1 | 7/2005 | Auer et al. | |
| 2005/0164320 A1 | 7/2005 | McDevitt et al. | |
| 2005/0249605 A1 | 11/2005 | Kane et al. | |
| 2006/0039009 A1 | 2/2006 | Kiesel et al. | |
| 2006/0046312 A1 | 3/2006 | Kiesel et al. | |
| 2006/0092413 A1 | 5/2006 | Kiesel et al. | |
| 2006/0121555 A1 | 6/2006 | Lean et al. | |
| 2006/0181710 A1 | 8/2006 | Kachanov et al. | |
| 2006/0182659 A1 | 8/2006 | Unlu et al. | |
| 2006/0193550 A1 | 8/2006 | Wawro et al. | |
| 2006/0268260 A1 | 11/2006 | Liu et al. | |
| 2006/0274313 A1 | 12/2006 | Gilbert et al. | |
| 2007/0009380 A1 | 1/2007 | Cunningham | |
| 2007/0070347 A1 | 3/2007 | Scherer et al. | |
| 2007/0076210 A1 | 4/2007 | Kiesel et al. | |
| 2007/0116609 A1 | 5/2007 | Baeuerle et al. | |
| 2007/0146704 A1 | 6/2007 | Schmidt et al. | |
| 2007/0147189 A1 | 6/2007 | Schmidt et al. | |
| 2007/0147726 A1 | 6/2007 | Kiesel et al. | |
| 2007/0148760 A1 | 6/2007 | Kiesel et al. | |
| 2007/0201025 A1 | 8/2007 | Greenwald | |
| 2008/0013092 A1 | 1/2008 | Maltezos et al. | |
| 2008/0013877 A1 | 1/2008 | Schmidt et al. | |
| 2008/0128595 A1 | 6/2008 | Kiesel et al. | |
| 2008/0181827 A1 | 7/2008 | Bassler et al. | |
| 2008/0183418 A1 | 7/2008 | Bassler et al. | |
| 2008/0186483 A1 | 8/2008 | Kiesel et al. | |
| 2008/0186488 A1 | 8/2008 | Kiesel et al. | |
| 2008/0186492 A1 | 8/2008 | Kiesel et al. | |
| 2008/0186494 A1 | 8/2008 | Kiesel et al. | |
| 2008/0186500 A1 | 8/2008 | Schmidt et al. | |
| 2008/0186503 A1 | 8/2008 | Kiesel et al. | |
| 2008/0186504 A1 | 8/2008 | Kiesel et al. | |
| 2008/0186508 A1 | 8/2008 | Kiesel et al. | |
| 2008/0187011 A1 | 8/2008 | Kiesel et al. | |
| 2008/0197272 A1 | 8/2008 | Kiesel et al. | |
| 2009/0156917 A1 | 6/2009 | Martini et al. | |
| 2009/0220189 A1 | 9/2009 | Kiesel et al. | |

FOREIGN PATENT DOCUMENTS

| | | |
|---|---|---|
| WO | WO 95/20144 | 7/1995 |
| WO | WO9954730 | 10/1999 |
| WO | WO0062050 | 10/2000 |
| WO | WO0201202 | 1/2002 |
| WO | WO2005108963 | 11/2005 |
| WO | WO 2006/133360 A2 | 12/2006 |
| WO | WO2009015723 | 2/2009 |

OTHER PUBLICATIONS

Kondziela, J., "Accurately Measure Laser Spectral Chracteristics," www.exfo.com, 2006, 5 pages.

Vogel, W., Berroth, M., "Tuneable liquid crystal Fabry-Perot filters", Institute for Electrical and Optical Communication Engineering, University of Stuttgart, 2002, 10 pages.

Adams, M. L., Enzelberger, M., Quake, S., and Scherer, A., "Microfluidic integration on detector arrays for absorption and fluorescence micro-spectrometers," Sensors and Actuators, 2003, pp. 25-31.

Office communication in U.S. Appl. No. 11/702,470, mailed Apr. 25, 2008, 22 pages.

Notice of Allowance and Fee(s) Due in U.S. Appl. No. 11/702,250, mailed Jun. 18, 2008, 11 pages.

Communiction from European Patent Office, including extended European search report with European Search Report and Annex and European search report opinion for counterpart EPO Application No. 08151022.4, dated Jun. 9, 2008, 7 pages.

Law, K.K., Coldren, L.A., and Merz, J.L., "Low-Voltage Superlattice Asymmetric Fabry-Perot Reflection Modulator", IEEE Photonics Technology Letters, vol. 3, No. 4, Apr. 1991, pp. 324-326.

Amendment in U.S. Appl. No. 11/702,470, submitted Jul. 25, 2008, 21 pages.

Office communication in U.S. Appl. No. 11/702,470, mailed Oct. 31, 2008, 22 pages.

Office communication in U.S. Appl. No. 11/702,363, mailed Sep. 4, 2008, 29 pages.

Amendment With Information Disclosure in U.S. Appl. No. 11/702,363, submitted Dec. 4, 2008, 34 pages.

Office communication in U.S. Appl. No. 11/702,249, mailed Aug. 7, 2008, 16 pages.

Amendement With Information Disclosure in U.S. Appl. No. 11/702,249, submitted Nov. 7, 2008, 30 pages.

Notice of Allowance and Fee(s) Due in U.S. Appl. No. 11/702,249, mailed Nov. 28, 2008, 9 pages.

Office communication in U.S. Appl. No. 11/633,302, mailed Sep. 5, 2008, 34 pages.

Amendment With Information Disclosure in U.S. Appl. No. 11/633,302, submitted Dec. 3, 2008, 34 pages.

Amendment in U.S. Appl. No. 11/702,470, submitted Jan. 30, 2009, 22 pages.

Notice of Allowance and Fee(s) Due in U.S. Appl. No. 11/702,470, mailed Apr. 24, 2009, 15 pages.

Notice of Allowance and Fee(s) Due in U.S. Appl. No. 11/702,363, mailed Mar. 23, 2009, 12 pages.

Office communication in U.S. Appl. No. 11/633,302, mailed Apr. 24, 2009, 17 pages.

Amendment After Final Rejection in U.S. Appl. No. 11/633,302, submitted Jun. 12, 2009, 32 pages.

Office communication in U.S. Appl. No. 11/702,328, mailed May 27, 2009, 28 pages.

Submission to European Patent Office for counterpart EPO Application No. 08151022.4, submitted Jul. 16, 2009, 16 pages.

Office communication in U.S. Appl. No. 11/702,328, mailed Dec. 2, 2009, 3 pages.

Amendment with Request for Continued Examination in U.S. Appl. No. 11/702,328, submitted Dec. 29, 2009, 24 pages.

Submission of Terminal Disclaimer in U.S. Appl. No. 11/633,302, submitted Dec. 4, 2009, 3 pages.

Notice of Allowance and Fee(s) Due in U.S. Appl. No. 11/633,302, mailed Dec. 30, 2009, 11 pages.

Office communication in U.S. Appl. No. 11/702,328, mailed Oct. 5, 2009, 23 pages.

Amendment After Final Rejection in U.S. Appl. No. 11/702,328, submitted Nov. 12, 2009, 22 pages.

Office communication in U.S. Appl. No. 11/702,320, mailed Aug. 12, 2009, 9 pages.

Amendment in U.S. Appl. No. 11/702,320, submitted Nov. 3, 2009, 24 pages.

Office communication in U.S. Appl. No. 11/702,329, mailed Aug. 24, 2009, 24 pages.

Amendment in U.S. Appl. No. 11/702,329, submitted Oct. 27, 2009, 23 pages.

Notice of Allowance and Fee(s) Due in U.S. Appl. No. 11/702,321, mailed Aug. 11, 2009, 20 pages.

Rule 312 Amendment in U.S. Appl. No. 11/702,321, submitted Oct. 27, 2009, 16 pages.

Office communication in U.S. Appl. No. 11/633,302, mailed Jul. 23, 2009, 5 pages.

Amendment with Request for Continued Examination in U.S. Appl. No. 11/633,302, submitted Jul. 23, 2009, 31 pages.

Amendment with Request for Continued Examination in U.S. Appl. No. 11/702,328, submitted Dec. 29, 2009, 24 pages.

Office communication in U.S. Appl. No. 11/702,329, mailed Feb. 1, 2010, 15 pages.

European Patent Office communication in EPO Application No. 08171499.0-2319/2072006, mailed Feb. 5, 2010, 1 page.

Office communication in EPO Application No. 08150964.8-1524, mailed May 7, 2010, 6 pages.

Office communication in U.S. Appl. No. 11/702,320, mailed Jun. 4, 2010, 29 pages.

Office communication in U.S. Appl. No. 11/702,328, mailed Jul. 22, 2010, 8 pages.

Office communication in U.S. Appl. No. 11/702,329, mailed Feb. 1, 2010, 15 pages.

Office communication in U.S. Appl. No. 11/702,320, mailed Feb. 24, 2010, 21 pages.

Amendment in U.S. Appl. No. 11/702,329, submitted Mar. 8, 2010, 26 pages.

Office communication in U.S. Appl. No. 11/702,329, mailed Mar. 19, 2010, 2 pages.

Amendment in U.S. Appl. No. 11/702,320, submitted Apr. 8, 2010, 26 pages.

Office communication in U.S. Appl. No. 11/702,320, mailed Apr. 15, 2010, 3 pages.

Amendment in U.S. Appl. No. 11/702,328, submitted Apr. 28, 2010, 21 pages.

Office communication in U.S. Appl. No. 11/702,328, mailed May 17, 2010, 9 pages.

Office communication in U.S. Appl. No. 11/702,329, mailed May 17, 2010, 19 pages.

Agilent Technologies, "HPLC-Chop/MS Technology", printed from internet Sep. 28, 2010.

McNichols et al., "Optical Glucose Sensing in Biological Fluids: an Overview", Journal of Biomedical Optics, Jan. 2000, vol. 5, No., 12 pages.

PSI, "Adaptive Infrared Imaging Spectroradiometer", printed from internet Sep. 28, 2010.

Nov. 7, 2005, Shah et al., "Optomechanical Design of Tunable InP-Based Fabry-Perot Filters for Wavelength Division Multiplexing Applications", J. Microlith., Microfab., Microsyst., vol. 4, Issue 4.

Sighn et al., Analysis of Cellular Structure by Light Scattering Measurements in a New Cytometer Design Based on a Liquid-Core Waveguide, IEE Proc Nanobiotechnol, Feb. 2004, 151(1):10-6.

Spear et al., "Low Noise Position Sensitive Detector for Optical Probe Beam Deflection Measurements", Review of Science Instruments, vol. 67, Issue 7, 1996.

Vollmer et al., "Multiplexed DNA Quantification by Spectroscopic Shift of Two Microsphere Cavities", Biophysical Journal, vol. 85, Sep. 2003, 1974-1979.

File History for U.S. Appl. No. 11/702,250 as retrieved from USPTO on Sep. 8, 2010, 173 pages.

File History for U.S. Appl. No. 11/702,363 as retrieved from USPTO on Sep. 8, 2010, 255 pages.

File History for U.S. Appl. No. 11/702,328 as retrieved from USPTO on Sep. 8, 2010, 559 pages.

File History for U.S. Appl. No. 11/702,470 as retrieved from USPTO on Sep. 8, 2010, 506 pages.

File History for U.S. Appl. No. 11/702,249 as retrieved from USPTO on Sep. 8, 2010, 233 pages.

File History for U.S. Appl. No. 11/702,329 as retrieved from USPTO on Sep. 28, 2010, 488 pages.

File History for U.S. Appl. No. 11/702,321 as retrieved from USPTO on Sep. 8, 2010, 322 pages.

Amendment in EPO Application No. 08171499.0-2319/2072006, submitted Jun. 21, 2010, 32 page.

File History for EP Application No. 08150966.3 as retrieved from European Patent Office Electronic File System on Feb. 10, 2011, 241 pages.

File History for EP Application No. 08151017.4 as retrieved from European Patent Office Electronic File System on Feb. 10, 2011, 234 pages.

File History for EP Application No. 08151020.8 as retrieved from European Patent Office Electronic File System on Feb. 10, 2011, 268 pages.

File History for EP Application No. 08150964.8 as retrieved from European Patent Office Electronic File System on Feb. 10, 2011, 244 pages.

File History for EP Application No. 08151019.0 as retrieved from European Patent Office Electronic File System on Feb. 10, 2011, 97 pages.

File History for EP Application No. 08151021.6 as retrieved from European Patent Office Electronic File System on Feb. 10, 2011, 203 pages.

File History for EP Application No. 08151022.4 as retrieved from European Patent Office Electronic File System on Feb. 10, 2011, 251 pages.

* cited by examiner

US 7,936,463 B2

CONTAINING ANALYTE IN OPTICAL CAVITY STRUCTURES

This application is related to the following co-pending applications, each of which is hereby incorporated by reference in its entirety: "Obtaining Analyte Information", U.S. patent application Ser. No. 11/316,303; "Position-Based Response to Light", U.S. patent application Ser. No. 11/633,302; "Photosensing Optical Cavity Output Light", U.S. patent application Ser. No. 11/702,250; "Encoding Optical Cavity Output Light", U.S. patent application Ser. No. 11/702,363; "Obtaining Information From Optical Cavity Output Light", U.S. patent application Ser. No. 11/702,249; "Distinguishing Objects", U.S. patent application Ser. No. 11/702,328; "Moving Analytes and Photosensors", U.S. patent application Ser. No. 11/702,470; "Implanting Optical Cavity Structures", U.S. patent application Ser. No. 11/702,329; "Tuning Optical Cavities", U.S. patent application Ser. No. 11/702,321; and "Tuning Optical Cavities", U.S. patent application Ser. No. 11/702,320.

BACKGROUND OF THE INVENTION

The present invention relates generally to techniques involving optical cavities that can contain analytes, such as optical cavities that provide output light to photosensing components and the output light can include information, such as about the analytes.

U.S. Patent Application Publication No. 2005/0164320 describes a system that includes a light source, a sensor array, and a detector. The sensor array is formed from a supporting member into which cavities such as Fabry-Perot type cavities may be formed. Chemically sensitive particles are positioned within the cavities, and may be configured to produce a signal when a receptor coupled to the particle interacts with the analyte.

It would be advantageous to have improved techniques for containing analytes in optical cavity structures.

SUMMARY OF THE INVENTION

The invention provides various exemplary embodiments, including products, systems, methods, apparatus, and devices. In general, the embodiments involve optical cavity structures that provide output light distributions to connected photosensing components and that contain analyte that affects the distributions.

These and other features and advantages of exemplary embodiments of the invention are described below with reference to the accompanying drawings.

DETAILED DESCRIPTION

Figure 1:
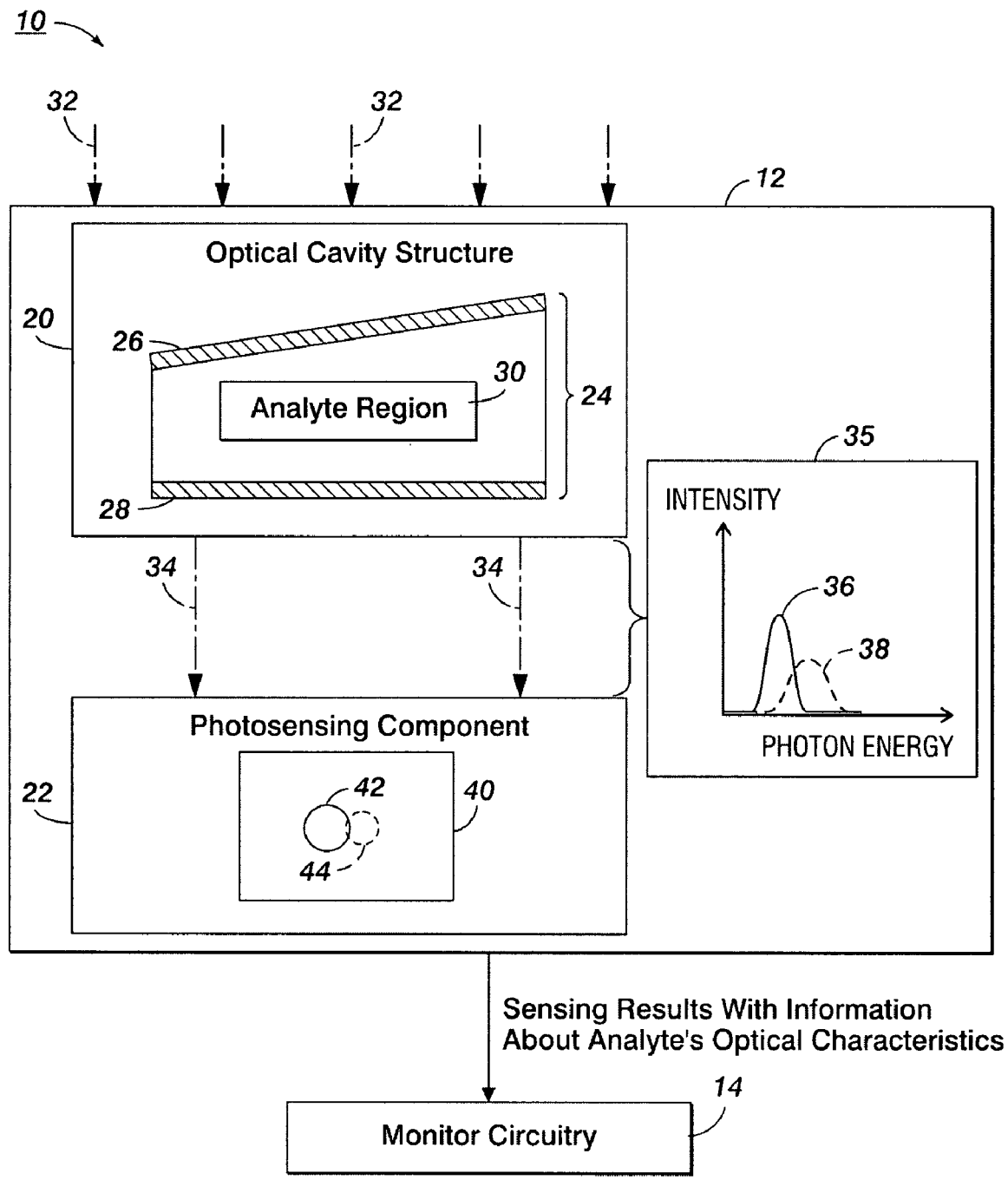
FIG. 1 is a schematic diagram of a system in which a structure that includes an analyte-containing inhomogeneous optical cavity is connected to a photosensing component.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum.

The term "photon" refers herein to a quantum of light, and the term "photon energy" refers herein to the energy of a photon. Light can be described as having a "photon energy distribution", meaning the combination of photon energies that are included in the light; highly monochromatic light, for example, has a photon energy distribution with one peak energy value. A photon energy distribution can be specified in space and time: For example, a photon energy distribution can be specified as a function of position, such as on a surface, or as a function of time; a photon energy distribution that is "homogeneous" is substantially the same at all relevant positions, such as the positions of a surface, while a photon energy distribution that is "stable" is substantially the same at all relevant times.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, light emitting diodes (LEDs), superluminescent LEDs (SLEDs), resonant cavity LEDs, sources of broadband light that is spectrally filtered such as with a monochromator, and so forth. A "tunable light source" is a light source that provides light with a predominant photon energy that can be changed in response to a signal or operation of some kind.

The term "laser" is used herein to mean any region, element, component, or device in which transitions between energy levels can be stimulated to cause emission of coherent light, such as in the ultraviolet, visible, or infrared regions of the spectrum. A "laser structure" is any structure that includes one or more lasers. A "laser cavity" is a region of a laser in which transitions can be stimulated to cause emission.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where light changes direction in a way that can be illustrated as a vertex between an incoming ray and an outgoing ray, the change may be referred to as a "reflection"; similarly, to "reflect" light is to cause the light to change its direction of propagation approximately at a surface, referred to herein as a "reflection surface". Where light propagates at less than c, it may be useful to obtain an "optical distance" of propagation; for any segment of length d in which speed of propagation is constant $\epsilon$*c, where $\epsilon \leq 1$, optical distance $D(\epsilon)=d/\epsilon$. An optical distance may be referred to herein as an "optical thickness", such as where light is propagating through a thickness of material.

To "photosense" is to sense photons, and to "photosense quantity" of photons is to obtain information indicating a quantity of the photons. Photons that are photosensed are sometimes referred to herein as "incident photons". A surface at which photosensing occurs is referred to herein as a "photosensitive surface".

A "photosensor" is used herein to refer generally to any element or combination of elements that senses photons, whether by photosensing quantity or any other information about the photons. A photosensor could, for example, provide an electrical signal or other signal that indicates results of sensing, such as a signal indicating quantity of incident photons; in general, signals from a photosensor that indicate results of sensing are referred to herein as "sensing results". If electrical sensing events occur in a photosensor in response to incident photons, the photosensor may integrate or otherwise accumulate the results of the electrical sensing events during a time period referred to herein as a "sensing period" or "sense period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described. A central wavelength or frequency or other value indicating a central photon energy of a range or subrange is sometimes referred to herein as a "central energy", and may be obtained in various ways, such as by finding an energy that has maximum intensity or that is another type of central value such as a mean or median of the distribution of light within the range or subrange.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry.

Circuitry can be described based on its operation or other characteristics. For example, circuitry that operates to monitor light is sometimes referred to herein as "monitor circuitry"; circuitry that performs control operations is sometimes referred to herein as "control circuitry"; and circuitry that performs processing operations is sometimes referred to herein as "processing circuitry".

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations of ICs described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An array may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

An IC includes a "photosensor array" if the IC includes an array of cells, and at least some of the cells include respective photosensors. A cell that includes a photosensor may also include "cell circuitry", such as circuitry that makes connections with the photosensor, that transfers signals to or from the photosensor, or that performs any other operation other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application of an IC that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry. Circuitry that responds to a photosensor could employ any suitable technique to read out photosensing results, including, for example, CCD, CMOS, or photodetector array (PDA) techniques.

An IC is or includes a "position-sensitive detector" or "PSD" if it includes a substantially continuous photosensitive surface and it provides electrical signals indicating a position resulting from a pattern of incident light on the photosensitive surface. For example, the signals could be two currents whose normalized difference is proportional to a centroid of the incident light pattern.

FIG. 1 illustrates general features of system 10, an example of a system that can be implemented as described in greater detail below. As with other implementations described below, system 10 involves a combination of parts or components. As used herein, a "system" is a combination of two or more parts or components that can perform an operation together. A system may be characterized by its operation: for example, an "analyte information system" is a system that operates somehow on analyte information; a "processing system" is a system that performs data or signal processing; and so forth.

Within a system, components and parts may be referred to in a similar manner. One component of an analyte information system in which information is obtained about an analyte's optical characteristics, for example, can be a "detector component" or simply "detector", meaning a component that detects light; similarly, a "light source component" includes one or more light sources; an "optical component" performs an optical operation; a "photosensing component" performs a photosensing operation; an "information obtaining component" obtains information, such as from photosensing results; an "adjusting component" performs an adjusting operation, such as on photosensing results; a "light-transmissive component" or simply "transmission component" transmits light; a "light-reflective component" or simply "reflective component" reflects light; and other examples are defined further below. Other parts or components can be characterized by their structure.

In the implementations described below, structures, systems, or parts or components of structures or systems may sometimes be referred to as "attached" to each other or to other structures, systems, parts, or components or visa versa, and operations are performed that "attach" structures, systems, or parts or components of structures or systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also making other types of connections such as electrical connections between or among devices or components of circuitry. A combination of one or more parts connected in any way is sometimes referred to herein as a "structure".

A structure may be described by its operation, such as a "support structure" that can operate as a support as described above; similarly, an "optical cavity structure" includes parts or components that can operate as an optical cavity; other examples are defined below. In addition, a structure may be characterized by the nature of its parts or the way in which they are connected; for example, a "layered structure" is a structure that includes one or more layers, and a "partial structure" refers to a structure that is in turn part of another structure.

System 10 includes device 12 and monitor circuitry 14. Device 12 in turn includes optical cavity structure 20 and photosensing component 22. Optical cavity structure 20 includes optical cavity 24.

The term "reflective optical cavity", or simply "optical cavity" or "cavity", refers herein to a light-transmissive region that is at least partially bounded by light-reflective components, with the light-reflective components and the light-transmissive region having characteristics such that a measurable portion of light within the light-transmissive region is reflected more than once across the light-transmissive region. An "optical cavity component" is a component that includes one or more optical cavities.

Within the broad category of optical cavities, there are various more specific types: For example, a laser cavity, mentioned above, is an example of an "emitting optical cavity" or simply "emitting cavity" that can operate as a source of emitted output light even when it is not receiving input light from an external light source, with the emitted light ordinarily resulting from a gain medium within the light-transmissive region; similarly, a "transmissive cavity" can operate, in response to input light from one or more external light sources at an entry surface, providing a transmitted portion of its output light at an exit surface different than the entry surface (a complementary, reflected portion may be provided at the entry surface); a "Fabry-Perot cavity" is a reflective optical cavity in which constructive interference (or positive reinforcement) occurs in one or more photon energy subranges while destructive interference occurs in others.

A Fabry-Perot cavity or other optical cavity that can operate to provide output light in one or more photon energy subranges while not providing output light with other photon energies may be described as having one or more "modes", each for a respective one of the output light energy subranges; if the cavity is a transmissive cavity, modes of its transmitted output light may be referred to as "transmission modes" and modes of its reflected output light may be referred to as "reflection modes". In the reflection spectrum, either the valley-like dips or the plateau-like reflection bands between the dips can be considered a "reflection modes". An emitting cavity can be described as "stimulated at" a mode by any operation that results in emission of output light in the mode's photon energy subrange. Similarly, a transmissive cavity can be described as "illuminated at" a mode by any operation that provides input light that results in transmission or reflection of output light in the mode's photon energy subrange.

In typical implementations of optical cavities, two light-reflective components have approximately parallel reflection surfaces and the light-transmissive region is sufficiently uniform that measurements would indicate many reflections of light within the light-transmissive region. Such cavities define a directional orientation as follows: Directions in which light could propagate and be reflected many times within the light-transmissive region are referred to herein as "reflection directions", and generally include a range of directions that are approximately perpendicular to both reflection surfaces. Directions that are approximately parallel to both reflection surfaces, on the other hand, are generally referred to herein as "lateral directions". In addition, the terms "in", "inward", or "internal" generally refer to positions, directions, and other items within or toward the light-transmissive region between the reflection surfaces, while "out", "outward", and "external" refer to positions, directions, and other items outside or away from the light-transmissive region. In general, it should be understood that the above directional orientation is arbitrary and only for ease of description, and that an optical cavity may have any appropriate orientation.

The above directional orientation does not in general apply to angle of incidence of input light. Transmissive cavities can typically operate in response to incident light that is not perpendicular to entry surfaces or reflection surfaces. Light incident on a transmissive cavity's entry surface at any angle is reflected multiple times within the cavity, producing transmission modes in accordance with the cavity's geometry. But transmission modes are affected by angle of incidence: Depending on the type of cavity and the angle of incidence, modes can be blue shifted or red shifted in comparison to perpendicular incidence; if all light enters a cavity at approximately the same angle, performance is affected only by the shifting of modes and modes are not also broadened, but performance is reduced if a cavity receives incident light distributed across a large angular range because transmission mode structure is then averaged over multiple angles.

Analyte is "present in", "positioned in", "contained in", or simply "in" an optical cavity when the analyte is in all or some part of the cavity's light-transmissive region; the optical cavity may be said to "contain" the analyte or to be an "analyte-containing optical cavity". An optical cavity provides "analyte-affected output light" if the optical cavity's output light is different in some way when analyte is present in the cavity than when analyte is absent, with the difference being due to the analyte's optical characteristics.

More generally, a cavity "includes a region" if the region is all or some part of the cavity's light-transmissive region. An "analyte region", therefore, is a region that can contain analyte.

The various exemplary implementations described below address problems that arise in obtaining information from output light of optical cavities, where the optical cavities contain analytes. The implementations are especially relevant to output light that includes information about an analyte's optical characteristics. One problem is previous techniques provide limited flexibility in how an optical cavity's output light is affected by the analyte's optical characteristics. Another is that some techniques include complicated combinations of components such as analyte-containing optical cavities, photosensing components, and laterally varying transmission components such as linearly varying filters (LVFs) on the photosensing components—it would be better to use less complicated combinations, possibly also allowing smaller devices that are more easily fabricated, less expensive, and more sensitive, with fewer sources of noise between an analyte-containing optical cavity and a photosensing component. In general, problems arise with technology that does not permit use of simpler components such as position-sensitive detectors (PSDs) instead of photosensor arrays; that has critical alignment requirements between components rather than relaxed alignment requirements; that requires a decoupling component rather than not having coupling problems.

As shown in FIG. 1, optical cavity 24 includes light-reflective components 26 and 28, and, between them, a light-transmissive region that includes analyte region 30. As suggested by the angle between the inner surfaces of light-reflective components 26 and 28, optical cavity 24 is inhomogeneous, with a "laterally varying energy output function", meaning that photon energies of output light depend on lateral position, such as in an exit surface of optical cavity 24. In response to input light, represented by arrows 32, optical cavity 24 provides output light, represented by arrows 34, at an exit surface of light-reflective component 28. The designation of surfaces as entry and exit surfaces can, however, be somewhat arbitrary, and it may be possible in some implementations to reverse direction of input and output light, to have multiple entry or exit surfaces, or to both receive input light through and provide output light at the same surface; the term "light interface surface" is therefore used herein as a generic term that includes any of these types of entry and exit surfaces.

With analyte present in analyte region 30, the laterally varying energy output function can be changed as a result of the analyte's optical characteristics, in which case optical cavity 24 has an "analyte-affected laterally varying energy output function", meaning that the function is different in some way when analyte is present in analyte region 30 than when analyte is absent, with the difference being due to the analyte's optical characteristics. As a result, the output light represented by arrows 34 is analyte-affected output light.

Box 35 contains a graph, showing examples of analyte-affected output light that could be provided if optical cavity 24 provides output light in modes. The graph shows an "intensity function", meaning that intensity of output light from a mode of optical cavity 24 can be represented as a function of another parameter, such as of photon energy or, in some implementations, of position.

An intensity function can have any of a wide variety of shapes and features, but a shape that frequently arises in transmission modes is the "peak", a shape characterized by a maximum value from which a curve for the function slopes steeply downward. Peaks have various features, including "central value", meaning the value of the other parameter at which the peak's maximum occurs, such as "central energy" for an intensity-energy function; "maximum intensity" or simply "maximum" or "amplitude", meaning the intensity value at the peak's maximum, whether measured as an absolute intensity or relative to another feature, such as a nearby minimum value; "contrast", meaning a value indicating relationship between magnitudes of the peak's maximum intensity and of one or more nearby minima of the transmission intensity function; and "intermediate intensity width", meaning the width of the peak at an intensity somewhere between its maximum and nearby minima, such as a full width half maximum (FWHM). In general, information can be encoded in one of these features in various ways, including those described in co-pending U.S. patent application Ser. No. 11/702,363, entitled "Encoding Optical Cavity Output Light" and incorporated herein by reference in its entirety. Once encoded, such information can also be recovered in various ways, including those described in co-pending U.S. patent application Ser. No. 11/702,249, entitled "Obtaining Information From Optical Cavity Output Light" and incorporated herein by reference in its entirety.

Information about an optical characteristic of analyte in analyte region 30 can be encoded in a mode's intensity function, such as by changing its central energy or changing its amplitude, its contrast, or its FWHM (or other intermediate intensity width), as indicated by dashed line 38 in the graph: Central energy of the intensity function for the illustrated mode is illustratively shifted from curve 36 to curve 38, such as by a change in refractive index; similarly, amplitudes, contrasts, and FWHMs of the intensity function of the mode are changed from curve 36 to curve 38, such as by changes in absorption. Curve 36 might be obtained, for example, with analyte absent, while curve 38 might be obtained with analyte present, changing refractive index and absorption spectrum of the optical cavity. More specifically, increasing absorption typically causes amplitude and contrast to decrease and FWHM to increase. Additional details about effects of refractive index and absorption and encoding techniques are provided in co-pending U.S. patent application Ser. No. 11/702,363, entitled "Encoding Optical Cavity Output Light" and incorporated herein by reference in its entirety.

In the illustrated example, photosensing component 22 includes photosensitive surface 40, which could be an array of photosensing cells or, in appropriate implementations, a position-sensitive detector (PSD). As a result of the laterally varying energy output function described above, the output light incident on photosensitive surface 40 has a "laterally varying photon energy distribution" or simply a "laterally varying energy distribution", meaning that photon energy of the light varies as a function of lateral position. Although one or more optical components could be included in device 12 between optical cavity structure 20 and photosensing component 22, additional optical components are likely to reduce the amount of information in the output light, such as by introducing noise. Therefore, a direct transfer of output light from optical cavity structure 20 to photosensitive surface 40 or, perhaps, transfer through an imaging component, would be most likely to optimize information content in sensing results from photosensing component 22.

Since device 12 is typically used to determine the laterally varying intensity distribution at the exit surface of inhomogeneous optical cavity 24, no components are required between structure 20 and photosensing component 22, especially if the two are directly attached. An imaging component might, however, enhance resolution by providing an enlarged image of the intensity distribution on the photosensitive component 22.

As suggested by the circles on photosensitive surface 40, the information about optical characteristics of analyte in the analyte-affected output light results in a difference in the laterally varying energy distribution on photosensitive surface 40. The laterally varying energy distribution when analyte is absent from analyte region 30 illustratively includes light spot 42, shown as a solid circle, but the distribution when analyte is present in analyte region 30 instead includes light spot 44, shown as a dashed circle. In the illustrated example, each light spot's circle might be obtained, for example, by comparing intensity at each position of photosensitive surface 40 with a threshold, in this case a threshold at a point on the vertical scale of the graph in box 35 at which the size of light spot 44 is smaller than that for light spot 42; various techniques can be used to obtain information about light spots.

The term "light spot" as used herein, refers to a distinguishable high intensity region of a pattern of light received by a photosensing component in response to which the photosensing component is capable of providing information about the light spot. For example, a photosensing component might provide information resulting from the higher intensity region's position, referred to herein as a "light spot position" or simply "spot position", or it might provide information resulting from the higher intensity region's extent on a photosensitive surface, referred to herein as "light spot size" or simply "spot size". Whether or not it is capable of providing information about light spot position and size, a photosensing component may also be capable of providing information resulting from the intensity of the higher intensity region, referred to herein as "light spot intensity".

In the illustrated example, light spot 44 is changed from light spot 42 in ways that resemble the changes from solid-line curve 36 to dashed-line curve 38 in the graph: Light spot 44 is shifted to the right, providing information about central energy shift of the mode's intensity peak. Similarly, light spot 44 has changed size in a way that reflects the width of peak 38 at the threshold intensity mentioned above; width at a given threshold tends to correlate with maximum intensity, and, if a change in width results from absorption, width at the given threshold also tends to vary inversely with change in FWHM (or other intermediate intensity width).

It should be noted that a photosensing component may be able to obtain information from a laterally varying energy distribution on photosensitive surface 40 even when the received pattern of light does not include distinguishable light spots. For example, where a photon energy subrange has a central energy, it is possible to obtain information resulting from the central energy's position, such as information about a position of maximum incident intensity, without distinguishing a light spot as such. Similarly, where a photon energy subrange can be localized within a respective region of a photosensitive surface, it is possible to obtain information resulting from intensity of light in the subrange, such as information about intensity of light incident on its region, without distinguishing a light spot.

In any case, photosensing component 22 provides sensing results with information about the analyte's optical characteristics. The information can include, for example, measurements of one or both of refractive index and optical absorption. Various other examples of types of information that could be obtained are mentioned herein, including measurements, spectra, derivatives, and information about whether an analyte is present or in what amount, density, concentration or other quantitative measure it is present.

In the implementation in FIG. 1, system 10 also includes monitor circuitry 14, connected to receive sensing results from photosensing component 22. Monitor circuitry 14 can therefore use the sensing results to monitor the analyte's optical characteristics, and could be implemented with a CPU obtaining analyte information as described below.

The general features in FIG. 1 could be implemented in many ways, as exemplified by the various implementations described below. In particular, the exemplary implementations below include several types of optical cavity structures illuminated in various ways, and many others could be employed in a system as in FIG. 8.

Also, photosensing component 22 could be implemented in many ways, including with various ICs that include devices with photosensitive surfaces that include discrete cells such as photosensor arrays, devices with continuous photosensitive surfaces such as PSDs, or any other type of photosensing components that can provide sensing results with information about an analyte's optical characteristics. For example, photosensing component 22 could be implemented as a one-dimensional photosensor array, and optical cavity structure 20 could be implemented as a coating over the array as described below. In addition, in some implementations, photosensing component 22 could be implemented as a PSD, as described in U.S. Patent Application Publication No. 2006/0039009, incorporated herein by reference in its entirety.

Photosensing components can obtain sensing results with information about analyte optical characteristics in various ways, including providing position-based or intensity-based output currents from a PSD, integrating current or accumulating free charge carriers in cells at different positions of an array, and various other techniques. In each case, the sensing results can be read out with appropriate techniques. While the output currents of a PSD or photodiode may in many cases be read out continuously, sensing results from cells of arrays are typically read out after sensing periods, such as with CCD or CMOS techniques.

A connecting component could connect optical cavity structure 20 and photosensing component 22 in any of a wide variety of ways. As noted above, structure 20 and component 22 could be connected as a result of a fabrication technique in which structure 20 is formed as a coating on photosensitive surface 40. Furthermore, various bonding, adhesive, or similar techniques could be used to make a similar connection between them. For implementations in which an air gap or other optical component between structure 20 and component 22 is appropriate, the connection can be made by spacers as suggested in FIG. 1 or by any other structure between, around, or otherwise positioned to hold structure 20 and component 22 in fixed positions spaced apart from each other. Both of them could be mounted on or attached to a connecting component in any appropriate way, some of which are described below.

Device 12 could be implemented with a wide variety of types of optical cavity techniques. In particular, optical cavity 24 could operate as an inhomogeneous cavity illuminated, for example, by multiple narrow band light sources, either in an array or fired in sequence, so that photosensed readout provides sampling points, e.g. for a refractive index and absorption value, for each of the light sources. If implemented as an inhomogeneous cavity similar to an LVF connected to provide its output light to a photosensor array, optical cavity 24 can have a cavity thickness suitable to a given number of output light modes; for example, it could be sufficiently thin to transmit only a single mode at each position, in which case it could be illuminated by a broadband light source adjusted to its spectral range.

The terms "broad band" and "narrow band" and related terms describing illumination of optical cavities are used herein with related meanings: For example, in the case of a laterally graded inhomogeneous transmissive cavity, light from a "narrow band light source" is transmitted as a light spot that cannot be treated as covering more than one position or location, while light from a "broadband light source" is transmitted across a sufficiently large area that different parts of the area can be ascribed to different photon energies or bands of photon energies. Under this approach, characterization of a light source as providing a broad band or a narrow band depends on characteristics of a cavity being illuminated and of photosensing components that receive its output light; depending on the gradient and FWHM of a coating or other graded cavity and on photosensing resolution, the light from a given light source (e.g. an LED) might be characterized as broad band in one context and as narrow band in another.

With a sufficiently steep gradient, a conventional LED's complete spectrum might be transmitted as a single, relatively small light spot relative to photosensing resolution, so that the LED would be characterized as a narrow band light source in this context. If the cavity contains analyte that affects its output light, a narrow band light source will produce a light spot with intensity and position that provide information about the analyte's optical characteristics in the narrow band of illumination.

On the other hand, with a sufficiently small gradient, the same LED's spectrum might be transmitted across a sufficiently large area that light transmitted at different positions or locations within the area can be separately photosensed, so that the LED would be characterized as a broadband light source in this context. If the cavity contains analyte that affects its output light, light transmitted at different locations within the large area can be analyzed separately to obtain energy-dependent information about the analyte's optical characteristics.

In general, characterization of a light source as broad or narrow band depends on the context, including characteristics of the cavity being illuminated and on photosensing resolution, which together with the light source's illumination band determine whether the resulting output light can be analyzed at multiple separate positions or ranges of positions, across a single range of positions, or only at a single position.

Optical cavity 24 could also be implemented with a tunable cavity, such as with deformable spacers, to set its wavelength range during manufacture or to adjust it during use, to provide a different set of sample points at each position. In any case, device 12 could be used in a system that applies referencing techniques to reduce the effects of noise and inhomogeneities, especially adjustment of measurements from the analyte cavity based on measurements from the reference cavity, but also possibly including contrast-based and other types of referencing as mentioned below.

Figure 2:
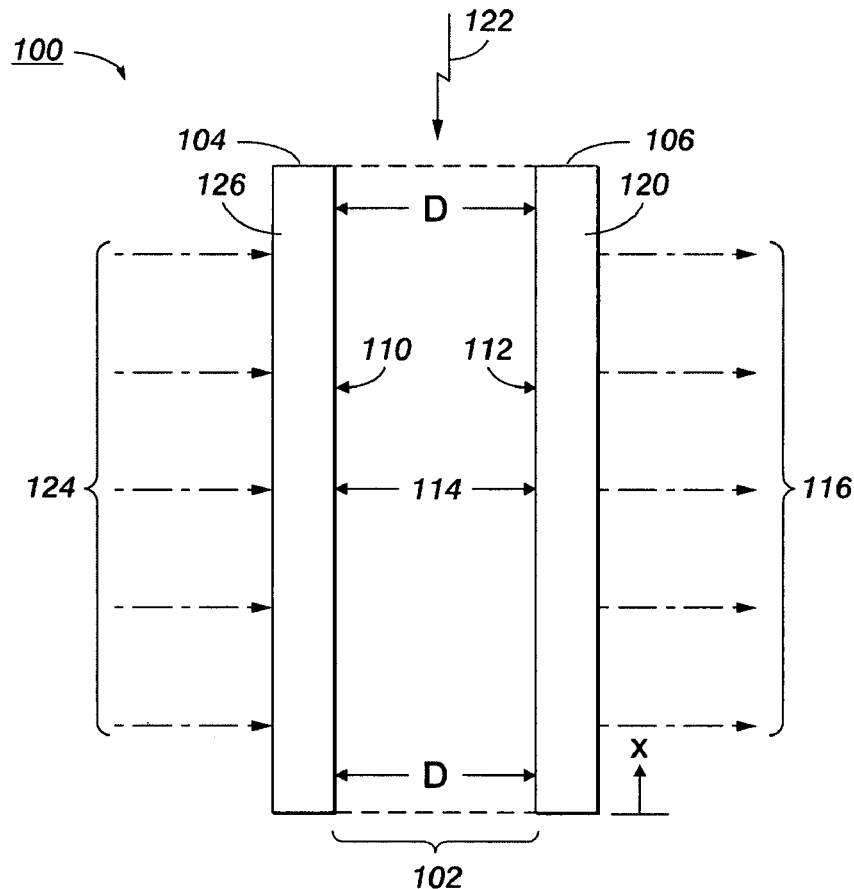
FIG. 2 is a schematic side view of a homogeneous optical cavity illustrating features that would also occur in optical cavities used in the system of FIG. 1.

FIG. 2 illustrates optical cavity 100, an example of a "homogeneous optical cavity", meaning a cavity whose light-transmissive region includes an extended part with substantially constant optical distance D between its reflection surfaces, sometimes referred to as its "homogeneous region". The homogeneous region of cavity 100 illustratively includes substantially all of light-transmissive region 102 where it is between and partially bounded by light-reflective components 104 and 106, though partially and completely bounded homogeneous regions with various other shapes and arrangements are possible.

Inward-facing surfaces 110 and 112 of components 104 and 106, respectively, can be implemented, for example, as mirrors or other reflective components that closely approximate the reflection surfaces of cavity 100. The characteristics of components 104 and 106 and of any material or structure within region 102 are such that a measurement would indicate that at least a portion of light within region 102 is reflected more than once. A reflection direction in which light can be repeatedly reflected between the reflection surfaces is represented by bidirectional ray 114, while one of the possible lateral directions in an x-y plane approximately perpendicular to ray 114 is illustrated by an x-axis at the lower right.

FIG. 2 also illustrates two ways in which homogeneous optical cavities can operate to provide output light, represented schematically by arrows 116. In both operations, output light can be provided at an exit surface, illustratively outward-facing surface 120 of component 106, which may or may not be approximately parallel to the reflection surfaces.

In the first operation, optical cavity 100 operates as an emitting cavity, such as a laser cavity. Typically, an emitting cavity operates in response to stimulation of some type, represented schematically in FIG. 2 by stimulation arrow 122. Stimulation arrow 122 could, for example, represent electrical or optical stimulation.

In the second operation, optical cavity 100 operates as a transmissive cavity, such as a Fabry-Perot interferometer. A transmissive cavity operates in response to input light from one or more external light sources, represented in FIG. 2 by illumination arrows 124. Input light can be received at an entry surface, illustratively outward-facing surface 126 of component 104, which also may or may not be approximately parallel to the reflection surfaces. As noted above, a reflected portion of output light can be provided at the entry surface, as described in greater detail below.

Figure 3:
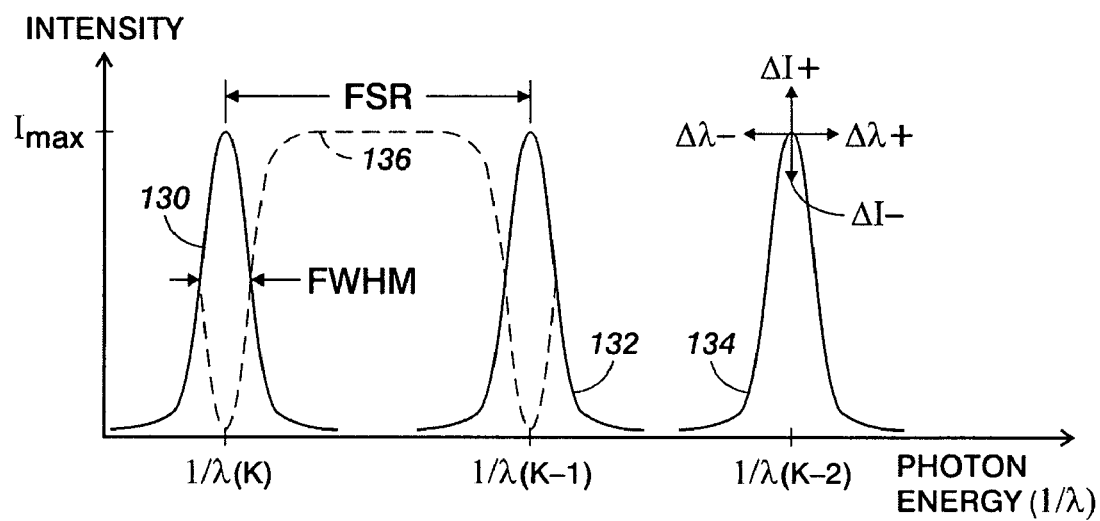
FIG. 3 is a graph showing intensity-energy curves for transmission and reflection from a cavity as in FIG. 2 when operated as a Fabry-Perot cavity, showing ways in which information can be included in transmission mode peaks.

FIG. 3 is an intensity-energy graph or "output spectrum" for optical cavity 100 when operated as a Fabry-Perot cavity such as an interferometer. Since photon energy is inversely proportional to wavelength, wavelength increases as one moves leftward along the horizontal axis, while the inverse of the wavelength ($1/\lambda$) increases as one moves rightward, as suggested by the labeling of points on the horizontal axis; it follows that energy and frequency would also increase to the right.

The graph in FIG. 3 includes a solid-line curve with peaks 130, 132, and 134, each of which is an "intensity-energy peak" or simply "intensity peak" that results from a respective transmission mode of cavity 100, illustratively the Kth, (K−1)th, and (K−2)th modes, and has an amplitude Imax, which could result from broadband illumination in the photon energy subranges of all the modes shown; such a curve is sometimes referred to herein as a "transmission spectrum". FIG. 3 also includes part of dashed-line curve 136 that is the complement of the transmission spectrum, i.e. the intensity-energy curve for light that is reflected rather than transmitted by optical cavity 100; such a curve is sometimes referred to herein as a "reflection spectrum" and its reflection modes are broad and separated by narrow valleys rather than being narrow peaks separated by broad valleys like the transmission modes. The term "output modes" is sometimes used herein as a generic term that encompasses transmission modes and reflection modes.

The maxima of intensity-energy peaks 130, 132, and 134 (and the complementary minima between reflection bands) are spaced apart as a function of photon energy (illustratively wavelength), and the difference between the central energy of adjacent transmission mode peaks is referred to as "free spectral range" or "FSR". FSR can be treated as the bandwidth over which adjacent intensity-energy peaks do not overlap, while the full width half maximum (FWHM) of the peaks can be treated as the minimum resolvable bandwidth. FSR, FWHM, and their ratio are all sometimes treated as figures of merit in designing a Fabry-Perot cavity.

The wavelength $\lambda$ of each intensity-energy peak can be obtained from $\lambda(k)=2nD/k$, where n is the refractive index of the cavity and k is a non-zero integer. Therefore, if refractive index of the cavity changes, $\lambda(k)$ also changes for a given value of k, so that if a peak's central energy changes, as indicated by $\Delta\lambda+$ and $\Delta\lambda-$ for peak 134, the change provides information about refractive index change. Similarly, the intensity of the peaks depends on absorption in the cavity, so that if the intensity of a peak departs from Imax, as indicated by $\Delta I+$ and $\Delta I-$ for peak 134, the change provides information about absorption change.

Figure 4:
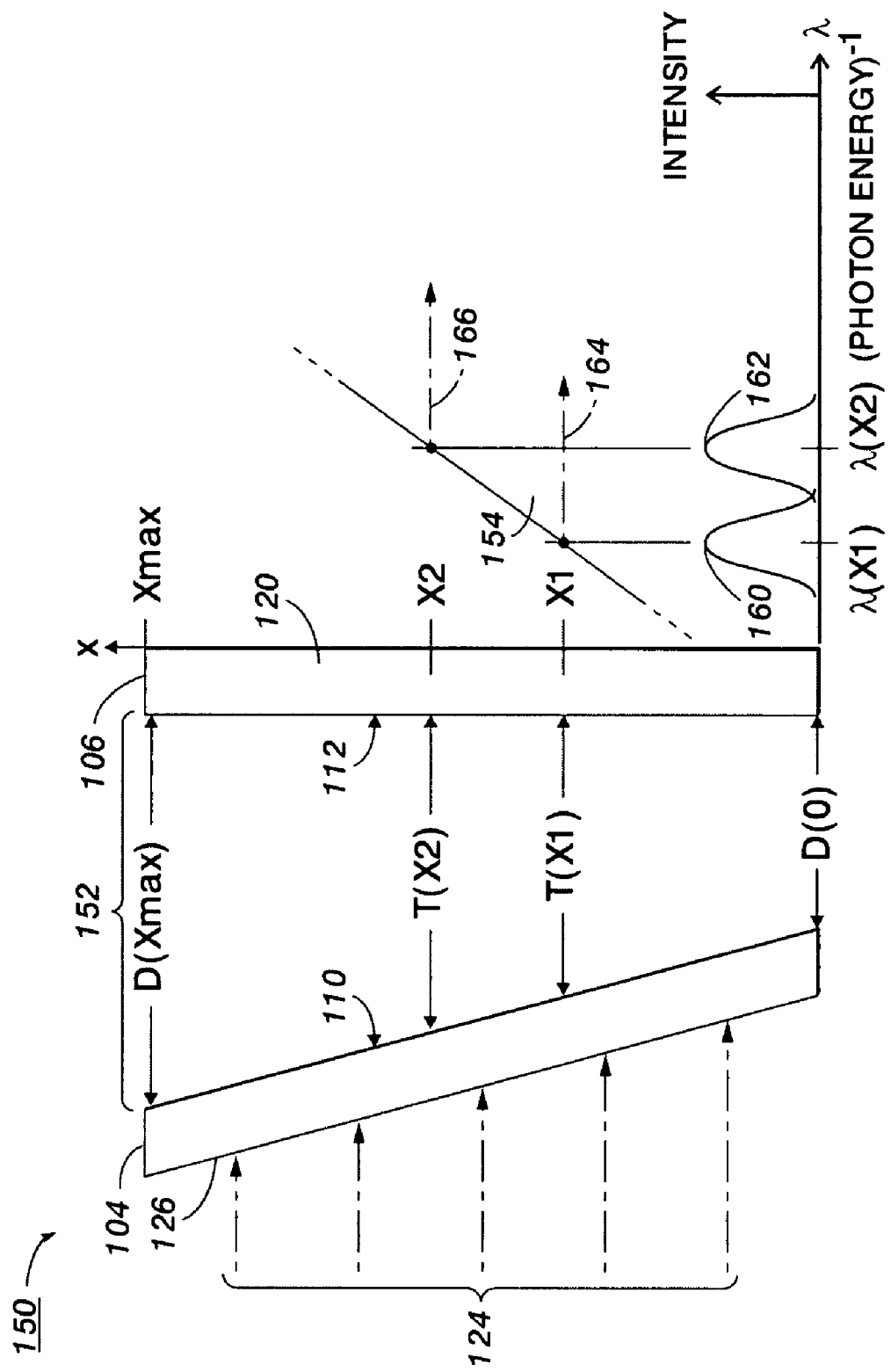
FIG. 4 is a schematic side view of a graded optical cavity that is an example of an inhomogeneous optical cavity that could be used in the system of FIG. 1.

FIG. 4 illustrates graded optical cavity 150, an example of an "inhomogeneous optical cavity", meaning a cavity that does not meet the above definition of a homogeneous optical cavity. Because of the similarities between cavities 150 and 100, parts and components of cavity 150 that are substantially the same as those in FIG. 2 are labeled with the same reference numbers. In cavity 150, however, region 152 is not homogeneous, but rather has "laterally varying optical distance" between reflective surfaces, meaning that the optical distance varies in one or more lateral directions; in the illustrated example, the optical distance illustratively increases linearly from D(0) at one end of cavity 150 (x=0) to D(Xmax) at the opposite end (x=Xmax), but optical distance between reflective surfaces in an inhomogeneous optical cavity could vary laterally in any appropriate way, and need not vary monotonically, linearly, or with any other type of uniformity.

Because of its linearly varying optical distance or thickness, cavity 150 can operate as a linearly variable optical filter or linear variable filter (LVF), a type of transmissive cavity. This capability is illustrated by the function T(x), a "laterally varying energy output function" meaning that photon energies of output light depend on lateral position; in this case, the function relates output photon energy (in response to input light represented by illumination arrows 124) to lateral position on exit surface 120. For an LVF, the simple relationship $\lambda(x)=T(x)=d'x+\lambda(0)$ can hold, where d' is a constant that depends on gradient of optical thickness and can be graphically represented by the constant slope $(\lambda(X2)-\lambda(X1))/(X2-X1))$ of position-wavelength graph 154 at right in FIG. 4.

In general, the characteristics of output light at each position on surface 120 can be a function of parameters other than optical thickness, including, for example, photon energy and incident direction of input light 124 received at counterpart positions on surface 126. In particular, the output light may depend on whether the input light is narrow band, broad band, or multi-modal, as can result from a set of transmission or reflection modes. Narrow band or multi-modal illumination of an LVF, for example, can produce one or several output light spots, respectively.

The graphs at right in FIG. 4 also illustrate intensity-energy peaks 160 and 162 that would result if cavity 150 were illuminated by narrow band input light with central energy of $\lambda(X1)$ and $\lambda(X2)$, respectively, and, in response, operated as an LVF as described above. At position X1, for example, T(X1) results in transmission of output light represented by arrow 164, within a photon energy subrange characterized by central energy $\lambda(X1)$; at position X2, T(X2) results in transmission of output light represented by arrow 166, within a photon energy subrange characterized by central energy $\lambda(X2)$; for the illustrated laterally varying energy output function, if $X1 \neq X2$ and the difference between X2 and X1 is sufficient, then $T(X1) \neq T(X2)$, and $\lambda(X1) \neq \lambda(X2)$. On the other hand, for relatively small regions of output surface 120, cavity 150 might in some cases operate locally as a homogeneous cavity with transmission modes as illustrated in FIG. 3. It follows that parameters applicable to transmission modes are sometimes also useful for intensity-energy peaks from inhomogeneous cavities; in particular, information about changes in refractive index and absorption can sometimes be provided through changes in intensity-energy peaks in ways shown in FIG. 3. Often, however, output light from an inhomogeneous cavity is more easily represented with an intensity-position graph, an example of which is described below.

Various techniques can be used to produce laterally varying energy distributions with inhomogeneous optical cavities having laterally varying optical thicknesses and, even with homogeneous optical cavities, with angled illumination from a point light source rather than perpendicular illumination; several techniques are described in co-pending U.S. patent application Ser. No. 11/316,438, entitled "Photosensing Throughout Energy Range and in Subranges" and incorporated herein by reference in its entirety. More generally, an inhomogeneous optical cavity can have any appropriate laterally varying energy output function, including functions that are nonlinear or nonuniform in other ways. Some of the below-described implementations, for example, involve functions that are affected by presence of an analyte in an optical cavity. As with homogeneous cavities, an inhomogeneous cavity's light-transmissive region can be completely between and partially bounded by light-reflective components as in FIG. 4, but partially and completely bounded light-transmissive regions with various other shapes and arrangements are possible.

Figure 5:
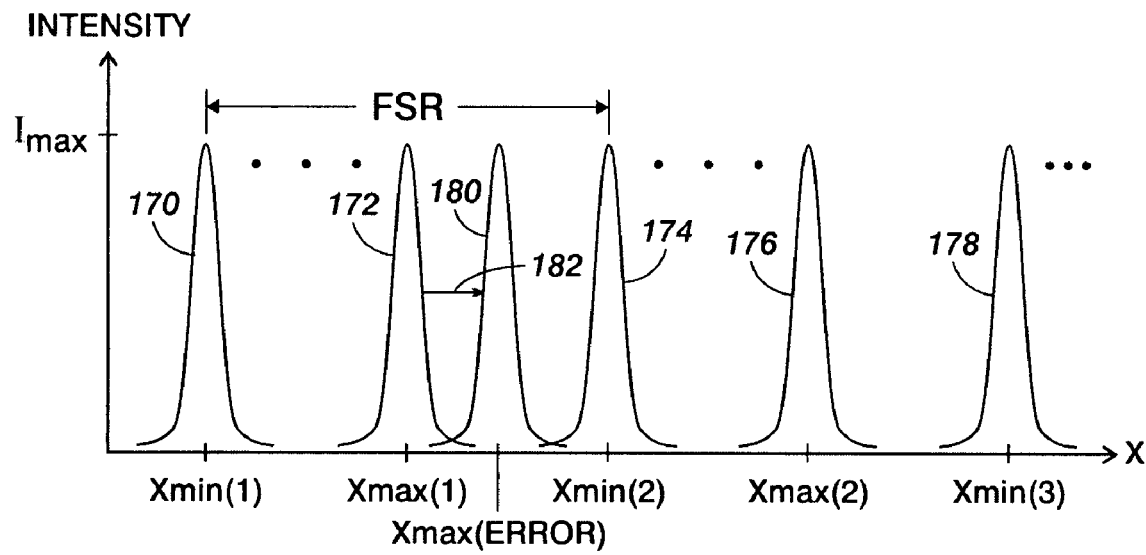
FIG. 5 is a graph showing an intensity-position function of a cavity as in FIG. 4, showing both spectral and harmonic relationships between peaks.

FIG. 5 is an intensity-position graph for optical cavity 150 when operated as a Fabry-Perot cavity such as an interferometer. FIG. 5 is similar to FIG. 3, and the peaks illustratively have maximum amplitude Imax as in FIG. 3 and their central energies and amplitudes (and FWHMs) could be affected as shown for peak 134 in FIG. 3, and their contrasts could also be affected; but the x-axis in FIG. 5 represents position in the x-direction in FIG. 4 rather than photon energy.

In the example shown in FIG. 5, cavity 150 is illuminated at P (P≧2) photon energies ranging from $\lambda$min to $\lambda$max, resulting in a series of output modes (illustratively transmission modes) for each photon energy $\lambda$(p) of illumination at those positions on the x-axis where the condition $\lambda(p)=2n*D(x)/k$ is satisfied for integer values of k. The first transmission mode shown for $\lambda$min is peak 170 at x=Xmin(1) and for $\lambda$max is peak 172 at x=Xmax(1). The second transmission mode shown for $\lambda$min is peak 174 at x=Xmin(2) and for $\lambda$max is peak 176 at x=Xmax(2). The third transmission mode shown for $\lambda$min is peak 178 at x=Xmin(3), and so forth.

In the example of FIG. 5, transmission modes are sufficiently separated along the x-axis to prevent interference between adjacent transmission modes. As can be seen, Xmin(2) is sufficiently greater than Xmax(1) that peaks 172 and 174 do not interfere, and Xmin(3) is similarly sufficiently greater than Xmax(2) that peaks 176 and 178 do not interfere. If instead the first transmission mode of $\lambda$max were peak 180 due to an increase from Xmax(1) to Xmax(error), as indicated by arrow 182, interference between peaks 180 and 174 would begin to occur; as the first transmission mode of $\lambda$max increased further, loss of information would occur due to ambiguity between peak 180 and peak 174. Problems of this type can be avoided by coordination of photon energy range with cavity parameters; for example, cavity thickness D can be sufficiently small that only one output mode occurs over the range from $\lambda$min to $\lambda$max. The free spatial range (FSR) between the modes in a particular wavelength range can also be increased by reducing the tilt of the inhomogeneous (graded) cavity.

Figure 6:
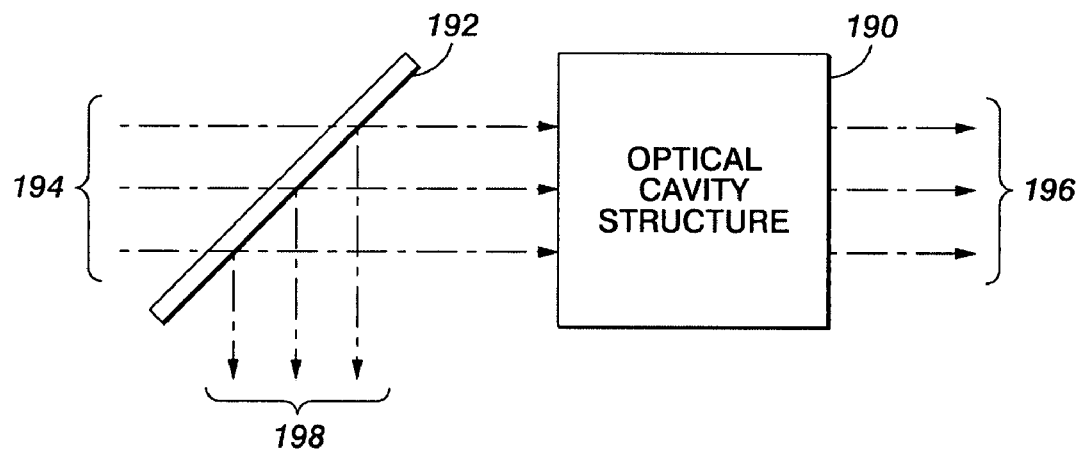
FIG. 6 is a schematic diagram of a setup in which an optical cavity as in FIG. 2 or 4 could operate to provide output light with reflection modes.

FIG. 6 shows a setup in which optical cavity structure 190 receives input light represented by arrows 192 through beam splitter 194. Optical cavity structure 190 can include a transmissive cavity implemented as in any of the ways described in relation to FIGS. 2-5 or in any other suitable way. In response to the input light, the cavity provides a transmitted portion of output light represented by arrows 196 and a reflected portion of output light represented by arrows 198. The use of beam splitter 194 is merely illustrative of ways in which input light and reflected light could be separated; for example, input light could be incident upon an entry surface at a sufficiently large angle from the normal that reflected light is separated from input light, though the non-perpendicular angle of incidence reduces performance of the optical cavity.

As suggested above in relation to FIG. 3, refractive index changes in the optical cavity will cause the same shift in both transmitted and reflected modes, while absorption in the optical cavity will similarly cause decreased amplitude and contrast and increased FWHM in both portions, with the effect of absorption typically varying as a function of photon energy; a curve showing absorption as a function of photon energy is sometimes referred to herein as an "absorption spectrum".

Figure 7:
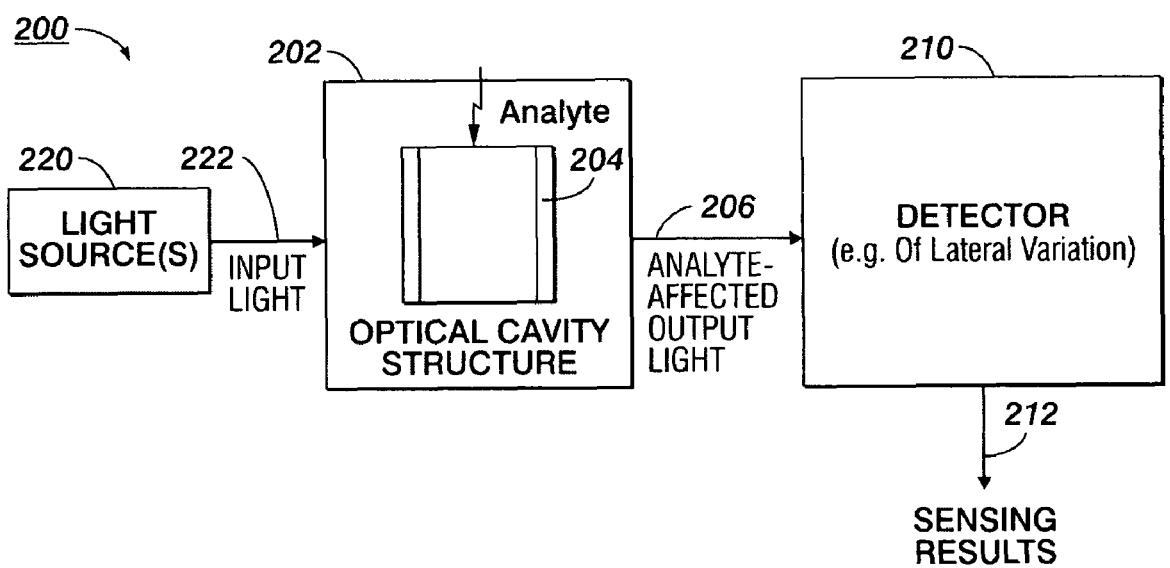
FIG. 7 is a schematic diagram of an implementation of the system of FIG. 1.

FIG. 7 shows system 200, an exemplary implementation of system 100 in FIG. 1. System 200 includes optical cavity structure 202, a structure that can include one or more optical cavities with features described above. In system 200, at least one of the optical cavities in structure 202, represented schematically by cavity 204, can contain an analyte, illustratively being provided to cavity 204. The presence of analyte in cavity 204 affects the output light provided by structure 202, and the analyte-affected output light, represented by arrow 206, can then be photosensed within detector 210. For example, detector 210 may include a photosensing component with one or more photosensitive surfaces at which lateral variation of light is detected, such as after the light passes through an LVF. The sensing results from detector 210 can be provided to other components within system 200 or to external components, as represented by arrow 212.

Detector 210 could be implemented in many different ways, such as with a photosensing IC, as described in co-pending U.S. patent application Ser. No. 11/702,250, entitled "Photosensing Optical Cavity Output Light" and incorporated by reference herein in its entirety. The implementation in FIG. 7 might, however, alternatively be implemented with photosensing components that do not include photosensing ICs, such as with one or more discrete photodiodes.

Although cavity 204 can be any suitable type of inhomogeneous optical cavity, including various kinds of transmissive cavities, FIG. 7 illustratively shows one or more light sources 220 that can be included within system 200 to illuminate one or more optical cavities. As represented by arrow 222, structure 202 receives input light from light sources 220. If optical cavity 204 is illuminated as shown, the analyte-affected output light represented by arrow 206 could include one or both of transmitted and reflected light.

Figure 8:
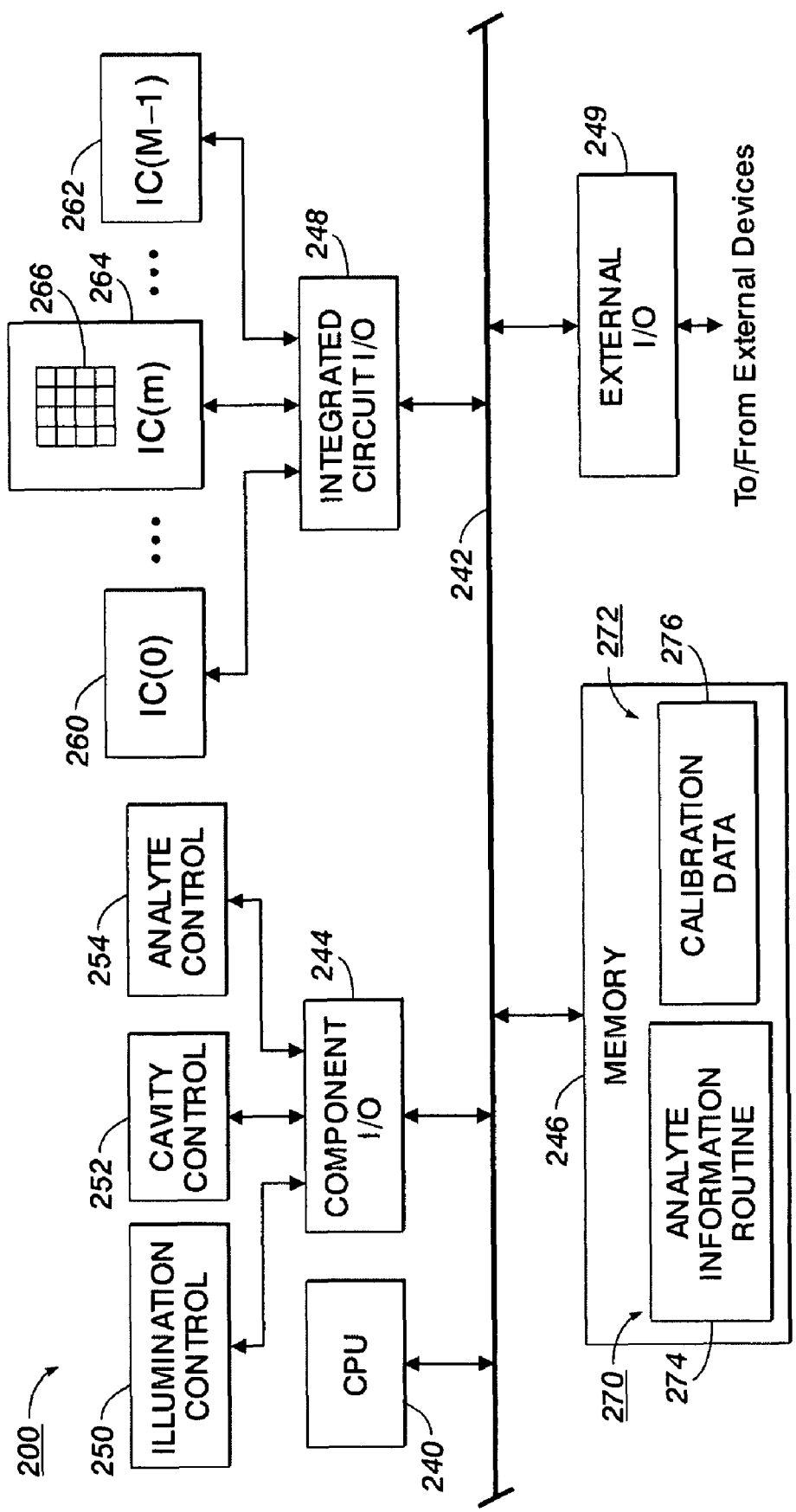
FIG. 8 is a schematic circuit diagram of a system implemented as in FIG. 7.

FIG. 8 illustrates electrical components that can be used in implementing system 200 as in FIG. 7. System 200 illustratively includes central processing unit (CPU) 240 connected to various components through bus 242, but a wide variety of other architectures could be employed, including any appropriate combination of hardware and software, as well as specialized hardware components such as application specific integrated circuits (ASICs) for one or more of the illustrated components or in place of a software component executed by CPU 240.

System 200 also includes component input/output (I/O) component 244, memory 246, integrated circuit input/output (IC I/O) 248, and external I/O 249, all connected to bus 242. System 200 can include various other components (not shown) connected to bus 242. In addition to connections through external I/O 249 by which signals can be provided to and received from external devices, bus 242 can also be connected directly to components outside of system 200.

Component I/O 244 permits CPU 240 to communicate with certain components of system 200, illustratively including illumination control 250, cavity control 252, and analyte control 254. For interactive applications, component I/O 244 could also be connected to a suitable user interface, such as a monitor and keyboard (not shown). In the exemplary implementation in FIG. 7, illumination control 250 can include light sources 220 (FIG. 7) and circuitry for controlling them; cavity control 252 can include electrodes or other components that can be operated to control cavity 204 and other cavities and can also include circuitry connected to those components; and analyte control 254 can similarly include fluidic devices or other components that can operate to transfer analyte into, through, or out of cavity 204 or other cavities or to produce relative movement between analyte and an array or a cavity, and can also include circuitry connected to those devices and components.

In the illustrated implementation of system 200, IC I/O 248 is a similar I/O component that permits CPU 240 to communicate with one or more ICs, such as in detector 210 in FIG. 5. M ICs are illustrated by a series from IC(0) 260 to IC(M−1) 262, including IC(m) 264 with a photosensor array 266.

Memory 246 illustratively includes program memory 270 and data memory 272, although instructions for execution by CPU 240 and data access during execution of instructions could be provided in any suitable way, including through external devices or components. The routines stored in program memory 270 illustratively include analyte information routine 274. In addition, program memory 270 could store various additional routines and also subroutines (not shown) that CPU 240 could call in executing routine 274. Similarly, the data in data memory 272 illustratively include calibration data 276, but could include various additional items of data and data structures accessed by CPU 240.

In executing routine 274, CPU 240 can provide signals to cavity control 252 and to analyte control 254 so that an analyte is present in cavity 204, for example, with the analyte having optical characteristics that affect output light from cavity 204. CPU 240 can also provide signals to illumination control 250 so that cavity 204 is appropriately illuminated to provide analyte-affected output light. CPU 240 can also provide signals to each of ICs 260 through 262 to obtain sensing results that include information about the analyte in cavity 204. In an implementation with a position-sensitive detector (PSD), CPU 240 could instead provide whatever signals are necessary to obtain photosensed quantities from the PSD; for example, CPU 240 could control circuitry to connect output currents from the PSD to a differential amplifier.

Figure 9:
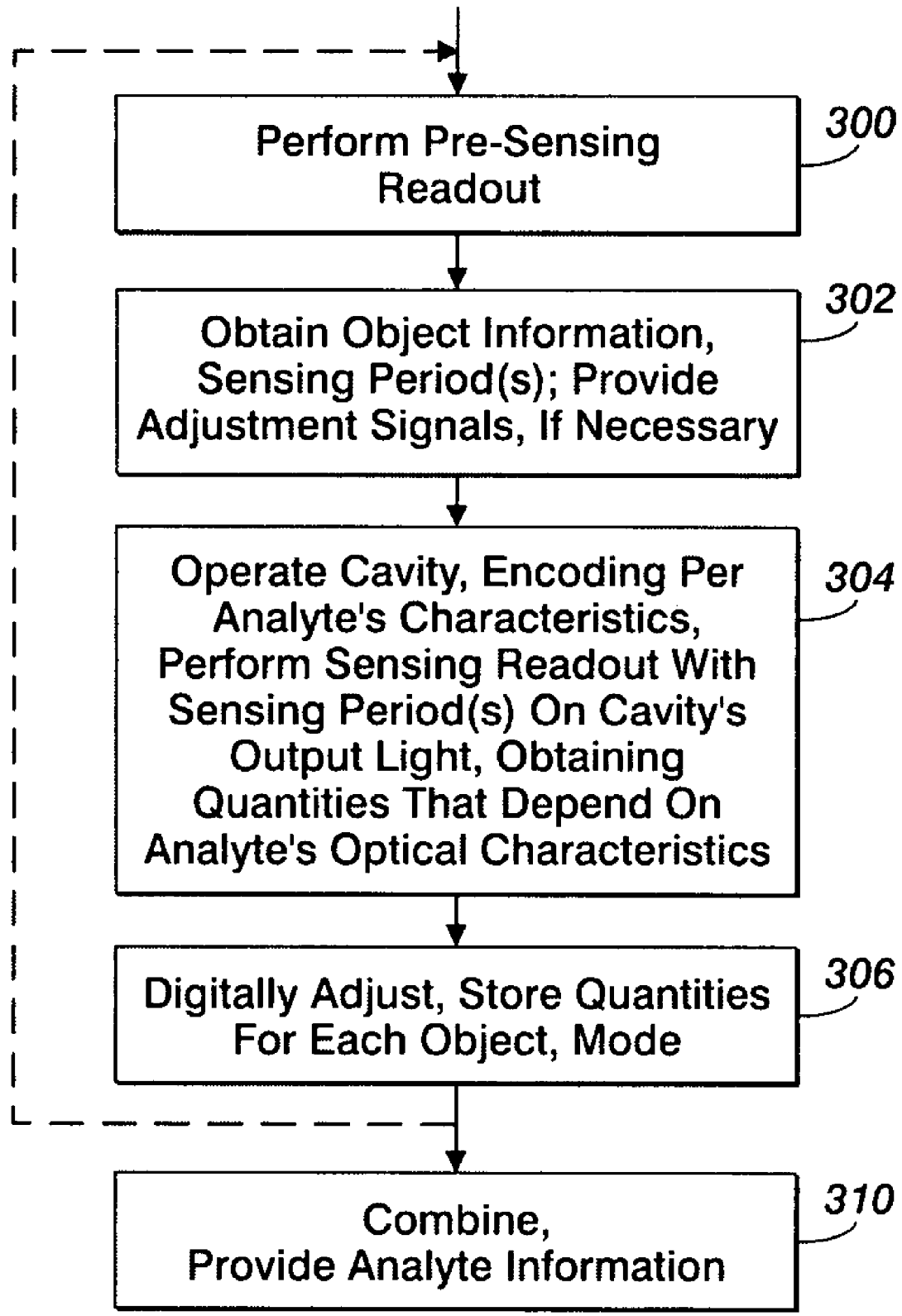
FIG. 9 is a flow diagram showing operations of the analyte information routine in FIG. 8.

FIG. 9 illustrates one example of how analyte information routine 274 could be implemented in a system like system 200 in FIGS. 7 and 8. The routine in FIG. 9 could be implemented for single objects moving along paths through cavities past arrays; for spaced multiple objects moving along paths through cavities past arrays; or for continuous streams of objects, such as small volumes of fluid, moving along paths through cavities past arrays, in each case subject to appropriate constraints and with the cavities providing laterally varying spatial intensity distributions that include information about analytes in objects.

Examples of objects that could occur in implementations as described herein include droplets, bubbles, small volumes of fluid, single molecules, agglomerated molecules, molecule clusters, biological cells, viruses, bacteria, proteins, DNA, microparticles, nanoparticles, and emulsions. A droplet or small volume of fluid may, for example, include atoms, molecules or other particles that affect refractive index, absorption, or other optical characteristics. An object "travels" or is caused "to travel" if the object moves through a succession of positions. For example, the object could be conveyed in a fluid, such as a liquid, gas, or aerosol, in which case the object may be referred to as being "carried by the fluid."

The term "path" is used herein to refer to a substantially continuous series of positions through which an object may travel. A path is "through a cavity" if an object following the path passes through part of the cavity. A photosensing component, such as an array or PSD, is "positioned along" or "along" a path through a cavity if the component is positioned near the cavity in such a way that, when an object following the path affects output light from the cavity, the photosensing component can obtain sensing results that include information about how the object is affecting the output light; it is not necessary, however, that the photosensing component be immediately against or adjacent to an external surface of the cavity that includes the path. An object following a path in a case where an array is along the path in any of these ways can be said to move "past the array".

The routine in FIG. 9 follows a general strategy of performing a series of readout operations, after which information is combined and provided. It would also be possible to provide the information from each readout operation immediately or to provide information both immediately after each readout operation and also after a series of readout operations.

When CPU 240 executes the operation in box 300, it performs a pre-sensing readout. The purpose is to obtain information necessary to later perform a sensing readout. The information could be obtained in the ways described in co-pending U.S. patent application Ser. No. 11/315,992, entitled "Sensing Photons from Objects in Channels" and incorporated herein by reference in its entirety.

Using the information from box 300, CPU 240 could obtain information about each object and determine an appropriate sensing period for each object, in the operation in box 302. For example, CPU 240 could perform calculations to determine whether one or more objects are present, the position of each object, and the speed of each object. Using this information and taking into account previously calculated sensing periods for the same objects, if any, CPU 240 can also determine an appropriate sensing period to be used during sensing readout; in general, the sensing period must provide an integration time shorter than the time necessary for an object to pass each cell in an array. Each object can therefore have a unique sensing period.

The operation in box 302 can also include providing any necessary signals through component I/O 244 to adjust movement of objects, such as by adjusting fluid speed; to adjust illumination or stimulation of the optical cavity; or to adjust characteristics of the optical cavity, such as by adjusting optical distances and/or tilt angles between light-reflective components. These signals could include any appropriate combination of signals to illumination control 250, cavity control 252, and analyte control 254. Tilt of the cavity could cause inhomogeneous flow, as described below.

CPU 240 can then cause operation of the cavity in a way that encodes information about the analyte's optical characteristics and can also perform sensing readout on a cavity's output light, in box 304. This operation includes providing any further signals through component I/O 244 so that the cavity provides analyte-encoded output light with laterally varying intensity distribution and also providing signals through IC I/O 248 so that photons are photosensed cumulatively during the sensing period obtained in box 302. During this operation, CPU 240 may also provide signals to peripheral circuitry on an IC so that analog quantities photosensed by cells are adjusted based on reference values. After adjustment, if any, analog quantities can be converted to digital signals for readout. The operation in box 304 can be implemented in whatever manner is appropriate for a given photosensing IC, whether a CCD or CMOS implementation, and regardless of whether readout is purely serial or is also parallel.

Since an analyte's optical characteristics can affect the output light provided from a mode of an optical cavity, such as in the ways described above in relation to FIGS. 1, 3, and 5, information about the optical characteristics is present in the cavity's output light, encoded in intensity functions of one or more modes and in a laterally varying intensity distribution. Sensing results obtained in box 304 can therefore include part or all of the encoded information, in the form of photosensed quantities that depend on the analyte's optical characteristics. For example, the sensing results can include information about at least one of position, size, and intensity of a light spot and, accordingly, about the respective mode's intensity peak. If the output light from the cavity includes intensity peaks for two or more modes, their respective light spots can be tracked separately as described below.

The photosensed quantities read out in box 304 can also be digitally adjusted by CPU 240 before being stored for each object and mode, in box 306. The digital adjustment can include adjusting quantities photosensed by cells based on reference quantities or based on calibration data 276 (FIG. 8), and can also include any necessary adjustments due to differences in sensing periods or other factors; calibration-based techniques that can be used are described in co-pending U.S. patent application Ser. No. 11/633,302, entitled "Position-based Response to Light" and incorporated herein by reference in its entirety.

The digital adjustment in box 306 and the analog adjustment, if any, in box 304 can also employ reference-based adjustment techniques similar to those described in co-pending U.S. patent application Ser. No. 11/316,438, entitled "Photosensing Throughout Energy Range and in Subranges" and incorporated herein by reference in its entirety; such reference-based adjustment techniques may be especially useful for intensity referencing and in tracking an object's position. In particular, such adjustments can be used to overcome problems with inhomogeneous illumination, but such techniques may be difficult to implement successfully in system 200 because external inhomogeneities that affect output light, such as in illumination or in stable or time-varying absorption by particles between light sources 220 and optical cavity 204, are not readily distinguishable from absorption within cavity 204. In other words, adjustment based on references may remove desired information about absorption changes inside cavity 204. Examples of reference channels are described below.

To avoid this and other such problems, the operation in box 306 or a subsequent operation can make an alternative data manipulation or adjustment to obtain "cavity-only absorption data", an expression that refers herein to values or other data in which information about absorption in cavity 204 is preserved while information is reduced about features exterior to cavity 204 such as inhomogeneities in illumination and external absorption, operating as described in co-pending U.S. patent application Ser. No. 11/702,249, entitled "Obtaining Information From Optical Cavity Output Light" and incorporated herein by reference in its entirety. As will be understood, the encoding of absorption information in the manner described allows removal of noise-like effects other than those from absorption coefficient inside cavity 204, influences such as external perturbations, disturbances, or inhomogeneities. As a result, measurements of absorption can have a higher signal to noise ratio. Also, information can be recovered from analyte-encoded output light that is selectively sensitive to absorption changes inside cavity 204.

Other adjustment techniques that can be used, such as in box 306, are described in co-pending U.S. patent application Ser. No. 11/702,329, entitled "Implanting Optical Cavity Structures", incorporated herein by reference in its entirety.

Orientation of components can result in non-perpendicular incidence of input light on optical cavities. Unless all output light is incident on one position of the detector component or the detector component has only a single large area as with some PSDs, adjustments can be made to correct for non-perpendicular incidence of input light: For example, if the light source component emits light from a point source at many different angles that are accordingly transmitted through the cavities at various angles, the detector component's photosensitive surface receives the output light at many different angles, but each cell of a photosensor array would receive only a very small angular distribution; therefore, if the angle could be known, as would be the case in a fixed geometry but may not be the case in FIG. 7, the angle-induced variation can be easily corrected.

The position and speed information about each object from box 302 can be used by the operation in box 306 to determine which photosensed quantities result from effects of each object. Similar techniques can be used to determine which photosensed quantities result from each mode's light spot when a cavity's output light includes two or more modes.

For homogeneous analyte in cavity 204 or for stationary or slow-moving objects in cavity 204, lock-in techniques could be applied to further improve signal to noise ratio, such as by modifying operations in boxes 302, 304, and 306 in FIG. 9. For example, illumination from light sources 220 can be modulated in order to modulate output light from cavity 204.

The applicable modulation frequencies would be constrained by the readout frequency achievable by detector 210. In implementations where it is not possible to directly record a correlation signal, a self-reference could be used, such as an empty channel in a fluidic structure or an uncoated reference cell in a photosensing array with coated cells to sense photon energy subranges.

In performing the operations in boxes 304 and 306, CPU 240 can employ data structures (not shown) stored in memory 246. For example, one data structure can store each object's previously calculated position and speed, which can then be used in performing subsequent calculations to identify effects of the same object; similarly, each object's data structure can also include each light spot's identifying information and the object's effect on the identified light spot, which can similarly be used in subsequent calculations. Also, a readout data structure can be employed to hold all of the adjusted quantity information about each object.

The operation in box 306 can update the readout data structure each time it obtains additional information about the same object. In an implementation as in FIG. 8, the operations in boxes 300, 302, 304, and 306 can be performed separately for each of ICs 260 through 262. Further, as suggested by the dashed line from box 306 to box 300, the same operations can be performed repeatedly for each of the ICs. If each object can be correctly identified throughout its travel along a path through cavity 204, the readout data structure can be used to hold all of the information obtained from all ICs. Between consecutive executions of the operations in boxes 300, 302, 304, and 306, the effects of each object may move only a few cells along the path, and consecutive objects must be sufficiently separated to avoid confusion. For example, each object may be a few μm in diameter, each cell may have a length along the path of between 10 and 20 μm, and consecutive objects may be two or three cell lengths apart. For larger objects or for cells of different sizes, the spacing between consecutive objects can be adjusted appropriately.

Various modifications could be made in the implementation of FIG. 9. For example, rather than being spaced apart, objects could be closer together. Even if several objects are having overlapping effects on a light spot, it may be possible to perform computational algorithms to separate the effects of the objects. Similarly, if objects are very close to each other but positioned along different cells, an optical structure between the path of the objects and detector 210 could ensure that photons affected by different objects travel to different cells; in this way, a continuous stream of objects could be measured. Furthermore, techniques as described above could be applied to a continuous fluidic stream without distinguishable objects in it, in which case the analyte-affected output light from optical cavity 204 would be determined by optical characteristics of concentrations of molecules in each position in the stream rather than by optical characteristics of distinguishable objects. In effect, the stream would be divided into imaginary small volumes, each of which would be an object analyzed as described above, allowing for continuous monitoring of how the output light from the fluid changes with time, such as due to changing composition of the fluid.

As the operations in boxes 300, 302, 304, and 306 are repeated while an object travels along a path past detector 210, more and more information is obtained, especially where a cavity's output light has more than one light spot, with each light spot having a respective position on the array. When the object has passed the whole array, information about the analyte it contains can be recomposed from the stored fractions.

Upon completion of any suitable amount of information gathering in boxes 300, 302, 304, and 306, CPU 240 can perform the operation in box 310 to provide analyte information, such as in the form of data for another routine or as output through external I/O 249. As shown, this operation can include combining the sensed quantities for each object so that analyte information for the object can be provided, such as in the form of an absorption spectrum, a value for the analyte's refractive index, or some other data structure.

Many possible uses exist for analyte information as obtained in box 310, and operations like those in FIG. 9 could be implemented with a wide variety of existing technologies; analyte information could be used, for example, to distinguish objects, as described in detail in co-pending U.S. patent application Ser. No. 11/702,328, entitled "Distinguishing Objects" or to detect glucose in bodily fluids, such as with techniques described in co-pending U.S. patent application Ser. No. 11/702,329, entitled "Implanting Optical Cavity Structures", both of which are incorporated herein by reference in their entireties. Furthermore, it is foreseeable that further uses of analyte information and technologies for implementing such operations will be developed in the future. In general, analyte information from box 310 can be used in any way whatsoever, including not only existing techniques but also techniques developed hereafter. The operations illustrated in FIG. 9 do not require any specific technology, such as for data storing or processing operation, and are compatible with any such technology that exists now or may be hereafter developed.

Figure 10:
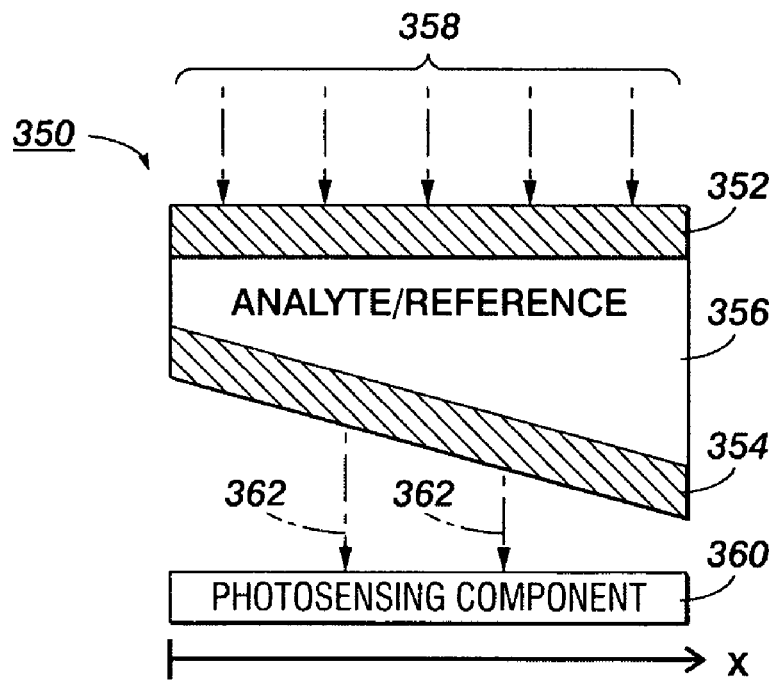
FIG. 10 is a schematic side view of a device that includes a graded optical cavity that can contain analyte and could be used in a system as in FIGS. 7 and 8.

FIG. 10 shows device 350, which can also be used in a system as in FIGS. 7 and 8. As shown, device 350 can include an inhomogeneous optical cavity, which could be illuminated during operation in any appropriate way, including with multiple narrow band light sources. Device 350 can also be implemented with a tunable optical cavity, as described in co-pending U.S. patent application Ser. No. 11/702,321, entitled "Tuning Optical Cavities" and incorporated by reference herein in its entirety. Light-reflective components 352 and 354 provide reflection surfaces on either side of region 356, which can include two containers, one containing analyte-containing fluid and the other reference fluid, as shown. As a result, when input light, represented by arrows 358, is received through component 352, inhomogeneous optical cavity operation as described in relation to FIGS. 4 and 5 can occur separately for each container, resulting in transmission of output light in one or more modes of each optical cavity to photosensing component 360. The indices of refraction of analyte and reference fluid in their respective parts of region 356 and the positioning of structures 352 and 354 determine positions of light transmission, and illumination in a single narrow wavelength band can be provided so that only one wavelength is transmitted from each optical cavity but at different output light positions for the two cavities due to their different optical characteristic. One way to operate the cavity is with narrow band illumination, in which case the analyte's optical characteristics affect where light is transmitted through the cavity and with what intensity. On the other hand, if broadband illumination is used, each cell of an array receiving the output light can have a respective energy range in which it receives light.

Figure 11:
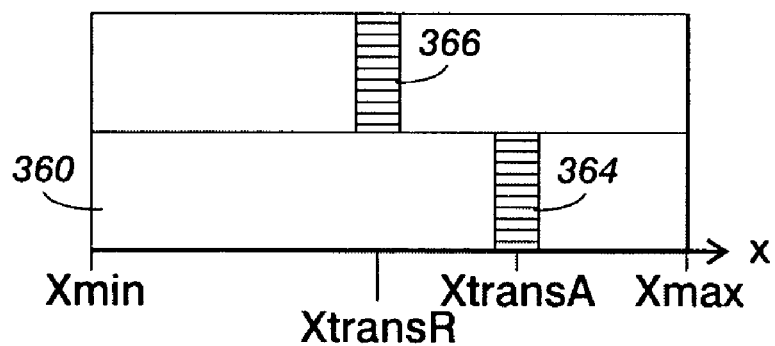
FIG. 11 is a schematic schematic top view of a photosensing component as in FIG. 10.

FIG. 11 shows an example of the pattern of light on the upper surface of photosensing component 360 if the optical cavities were both illuminated in only one narrow wavelength band. As shown, light spot 364 on the analyte cavity side of photosensing component 360 indicates that the incident narrow band light is transmitted at a certain position XtransA from the analyte cavity, but the same narrow band is transmitted from the reference cavity at a different position in the x-direction, displaced from XtransA either toward Xmin (as shown by light spot 366 on the reference cavity side of photosensing component 360 at XtransR) or toward Xmax, depending on the difference between refractive indices of analyte and reference fluids. If analyte absorption changes, causing a change in intensity, contrast, and FWHM of output light's intensity function from the analyte container, the size and intensity of light spot 364 would change relative to light spot 366. In this way, the difference in the intensity functions of the two light spots provides information about the refractive index and absorption of the analyte.

Inhomogeneous optical cavities that contain analyte can be implemented in many ways in addition to the way illustrated in FIGS. 10 and 11. In many applications, an optical cavity structure as in FIGS. 1 and 7 could be implemented to include one or more inhomogeneous optical cavities that contain analyte as in FIGS. 10-11. Furthermore, the optical cavity in device 350 could instead be a homogeneous optical cavity that contains analyte and that is operated to provide a laterally varying output energy distribution, by providing a range of angles at which input light is incident, as described in co-pending U.S. patent application Ser. No. 11/316,438, entitled "Photosensing Throughout Energy Range and in Subranges" and incorporated herein by reference in its entirety.

Figure 12:
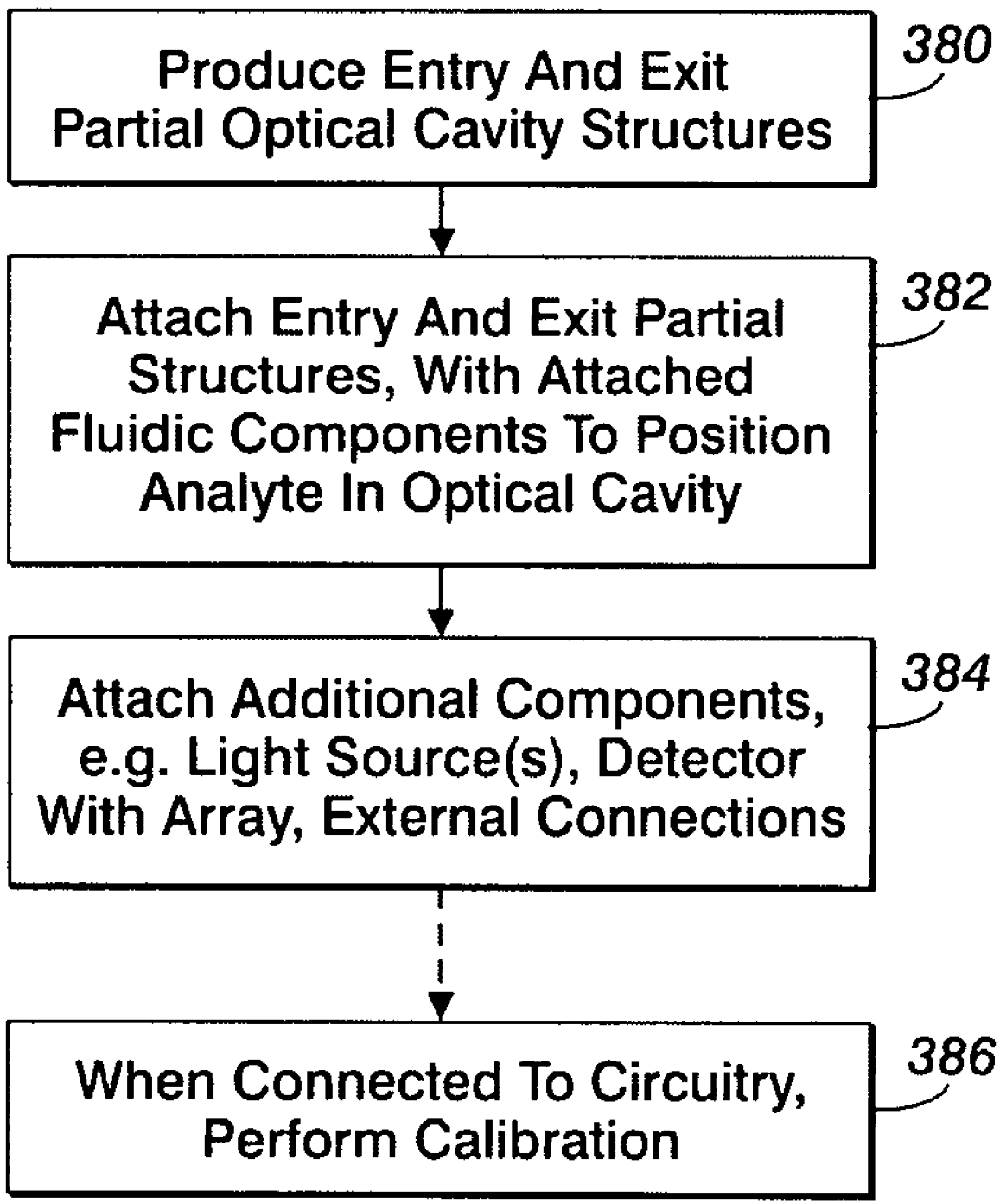
FIG. 12 is a flowchart showing operations in producing devices as in FIGS. 10 and 11.

FIG. 12 illustrates exemplary operations in producing a device like device 350 in FIGS. 10 and 11. In particular, the operations in FIG. 12 make it possible to produce apparatus in which an analyte-containing optical cavity occurs in a coating on top of a photosensing IC, allowing increased sensitivity and compactness of an optical sensor of analyte optical characteristics.

The operation in box 380 in FIG. 12 produces entry and exit partial optical cavity structures. This operation can include producing an entry light-reflective component on an entry glass and also producing an exit light-reflective component on an exit glass. Similarly, this operation can include producing an entry light-reflective component on an entry glass and also producing a transmission structure and an exit light-reflective component on a photosensing array. This operation can also include producing a patterned layer of SU-8 or polydimethylsiloxane (PDMS) on one or both of the light-reflective components, such as with techniques described in co-pending U.S. patent application Ser. No. 11/315,992, entitled "Sensing Photons from Objects in Channels" and incorporated herein by reference in its entirety. This patterned layer could include structures such as spacers and walls, dimensioned and positioned to ensure that the resulting optical cavity has the desired dimensions to satisfy various constraints, such as with appropriate grading as shown in FIG. 10 or other desired inhomogeneity. At the same time, dimensions must be chosen that can produce the desired optical cavity modes over the desired range of photon energies with the available illumination, such as to obtain an absorption spectrum or to measure refractive index dispersion; for example, the number of modes depends on the distance between reflection surfaces bounding the cavity. Therefore for implementation with inhomogeneous cavities, a thin cavity thickness can be chosen, which also allows also for operation in spectral regions with higher background absorption. In an example for glucose monitoring, it might be desirable to use the spectral region between 7 and 11 μm in which glucose shows very characteristic glucose absorption peaks but unfortunately also the water background absorption is much higher than in other interesting spectral regions. For example, in the spectral region around 2.2 μm, the water absorption is lower by about a factor of 200, but glucose has a much lower and less specific absorption.

If appropriate, an anti-adhesive coating can be applied to interior channel surfaces, such as by dip-coating polyethylene glycol (PEG) or by providing a coating of parylene C or vapor deposited tetraglyme.

The operation in box 382 then attaches the entry and exit partial structures, with attached fluidic components to position analyte in the resulting optical cavity. The operation in box 382 can include forming a suitable bond between the entry and exit partial structures so that they are firmly attached to each other. Also, the fluidic components attached to the resulting optical cavity structure can include, for example, connectors, tubing, pumps, sensors, and so forth; it is important that the combination of fluidic components be capable of operating to cause and control positioning of analyte within the optical cavity, such as by carrying the analyte into the optical cavity with a fluid or in some other way. The operation in box 382 can also optionally include attachment of wires or other appropriate circuitry connected, for example, to the photosensing array.

The operation in box 384 then attaches any other additional components necessary to complete the device. For example, if the device includes light sources, these components can be attached by the operation in box 384. Similarly, if a photosensing array is not part of the exit partial structure, the photosensing component can be attached by the operation in box 384. The operation in box 384 can also include any other external electrical, optical, or fluidic connections necessary for operation of the device. Alternatively, such connections could later be made when the device is incorporated into a system, such as system 200 in FIGS. 7 and 8.

The choice of a detector can be made based on several constraints. For example, if intensity peaks of a small number of modes are photosensed to detect changes in central energy or position, amplitude, contrast, and FWHM, it may be possible to use a respective one-dimensional photosensing array for each optical cavity, with each array including a relatively small number of cells, reducing the electrical power requirement because less power is dissipated in the detector. In general, compactness is promoted by using a photosensing IC, as described in co-pending U.S. patent application Ser. No. 11/702,250, entitled "Photosensing Optical Cavity Output Light" and incorporated by reference herein in its entirety.

The operation in box 386 can be performed at any appropriate time after the other operations, as suggested by the dashed line from box 384 to box 386. In addition, the operation in box 386 performs calibration, which requires that components be appropriately connected to circuitry, such as in the ways illustrated in FIGS. 7 and 8. The necessary connections could be created as part of the operations in boxes 380, 382, and 384 or instead could be created after the operation in box 384 and before performing calibration. In any case, calibration in box 386 can include obtaining items of data or data structures to be used in obtaining analyte information as described herein, and the data or data structures can be stored in memory 246 as part of calibration data 276 (FIG. 8), or, in appropriate cases, can be embedded in analyte information routine 274 or stored in another appropriate form.

In general, the operations in any of boxes 380, 382, 384, and 386 can include additional activities. For example, at any appropriate point in production of the device, wires or other appropriate circuitry can be attached to provide signals to or from a microprocessor or input/output (I/O) device to pumps and other fluidic components or to provide signals from a photosensing array to a microprocessor or I/O device. Similarly, connections can be made at any appropriate time to provide power. Also, it might be possible to precisely tune optical cavity dimensions, such as using techniques as described in co-pending U.S. patent application Ser. No. 11/702,321, entitled "Tuning Optical Cavities" and in co-pending U.S. patent application Ser. No. 11/702,320, entitled "Tuning Optical Cavities", both of which are incorporated by reference herein in their entireties.

The technique of FIG. 12 could be modified in many ways within the scope of the invention. For example, the operations in boxes 380, 382, and 384 could be combined in any appropriate way to facilitate attachment of components in a desired sequence. Also, an additional operation could be performed to align or attach interconnects between ICs, gates, and other circuitry, such as connectors to a microprocessor or computer, or this operation could be partially performed in each of boxes 380, 382, 384, and 386. Furthermore, the technique of FIG. 12 is extremely general, and could be employed to produce a wide variety of different devices that encode information about optical characteristics of analyte within an optical cavity and obtain sensing results indicating the optical characteristics. Examples described above show how objects can be carried through a channel within an optical cavity while such operations are performed, but various other arrangements are possible, some examples of which are described below.

Figure 13:
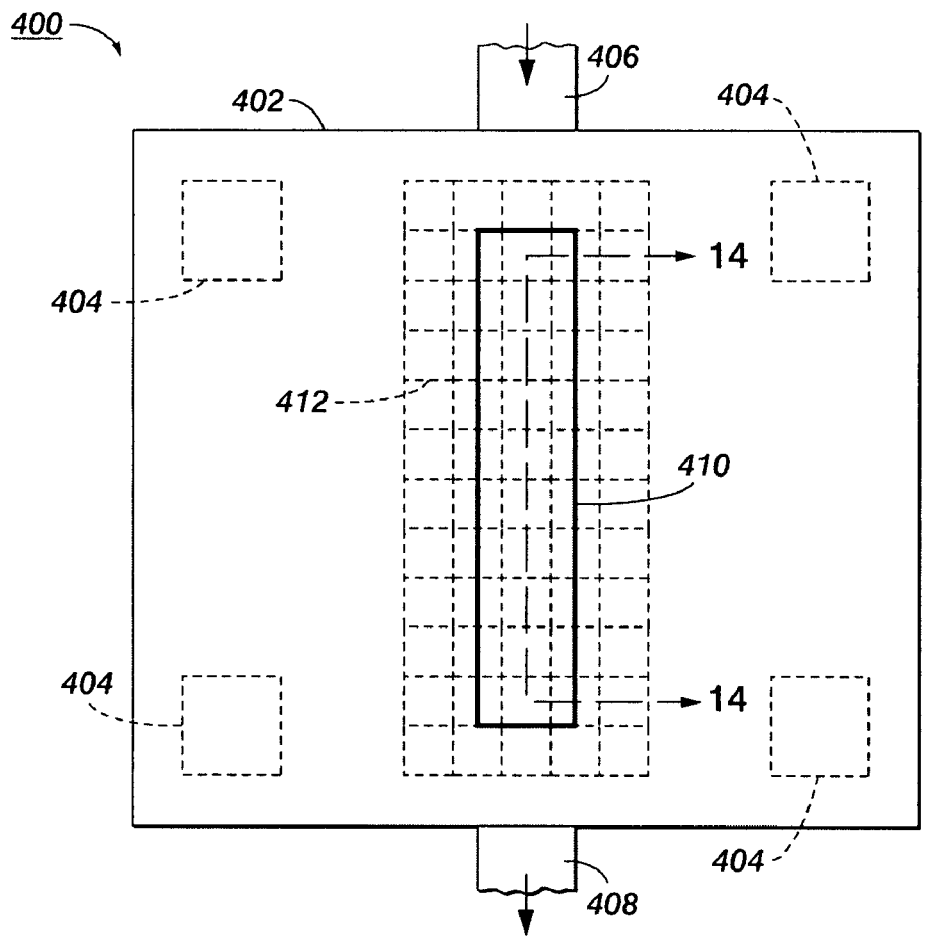
FIG. 13 is a schematic top view of an implementation of a device as in FIGS. 10 and 11.

FIG. 13 shows device 400, which could be used in an implementation of system 200. Entry glass 402 and an exit glass (not shown) are of substantially the same size and shape, and their inward-facing surfaces have coatings or other structures that function as light-reflective components, reflecting light into a light-transmissive region between them to operate as an optical cavity. The two glasses are illustratively separated by spacers 404 and the light-transmissive region may also contain fluidic walls or other structures (not shown) that bound a duct or channel between inlet 406 and outlet 408; as a result, an analyte or a fluid carrying an analyte can enter the optical cavity from inlet 406, can be carried along a path through the optical cavity such as through a duct or channel, and can then exit from the optical cavity to outlet 408.

Over or on entry glass 402 is light source component 410, which can include one or more light sources such as lasers, LEDs, resonant cavity LEDs or super luminescence diode (SLDs), a spectrally filtered broadband light source, or arrays of light sources, to illuminate the optical cavity. Photosensing component 412 is on the underside or below the exit glass, positioned along the analyte's path through the optical cavity. Light source component 410, photosensing component 412, and the optical cavity between them have characteristics such that the optical cavity responds to illumination from the light sources by providing analyte-affected output light with a laterally varying energy distribution that includes information about analyte optical characteristics. The output light can be photosensed by photosensing component 412, which can be implemented as a photosensing array, such as on an IC.

Figure 14:
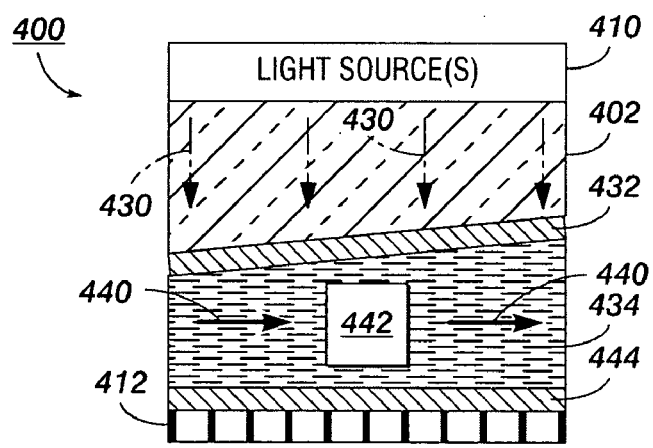
FIG. 14 is a schematic cross section of the device of FIG. 13, taken along the line 14-14.

FIG. 14 shows a longitudinal cross-section of device 400, viewed along the line 14-14 in FIG. 13. In the illustrated cross-section, light sources 410 are providing light, represented by arrows 430, which passes through entry glass 402 and through entry light-reflective component 432 before entering channel 434. Within channel 434, a moving fluid such as a liquid, gas, or aerosol, represented by arrows 440, carries an object 442. While object 442 is present in the optical cavity, its optical characteristics can affect light reflected within channel 434 between entry light-reflective component 432 and exit light-reflective component 444. As a result, analyte-affected output light exits through exit light-reflective component 444 and is directly photosensed by photosensing component 412.

In general, object 442 can be a particle, droplet, or small volume of fluid that can be carried by a fluid or other appropriate substance and that includes an analyte to be analyzed. The term "object" is used herein in the general sense of any distinguishable thing that can have optical characteristics such as refractive index and absorption. More generally, any optical loss mechanism within the optical cavity could affect transmitted and reflected intensity, whether resulting from absorption, scattering, or reflection (e.g. at the interface of a larger object) in another direction. Any of these loss mechanisms would contribute to the cavity loss, affecting intensity, contrast, and FWHM (and other intermediate intensity widths) of the cavity's output modes. Although scattering and reflection losses do not show a pronounced photon energy dependence and therefore only provide a loss background without much specific information, absorption often shows a distinct spectral dependence for a particular analyte, especially in the mid- and far-infrared ranges where molecules show absorption due to distinct vibrational and rotational states and overtones.

The terms "fluidic structure" and "channel" are used herein with related meanings: A "fluidic structure" is a structure that depends for its operation on fluid positioning or fluid flow, such as, for liquids or gases, in response to pressure or, for liquids, as a result of surface tension effects; a "channel" is any tube or other enclosed passage defined within a fluidic structure and through which fluid flows during operation. The direction in which fluid flows within a channel is sometimes referred to herein as a "flow direction."

It might be possible to modify device 400 to also include a transmission structure between the optical cavity and array 412, such as an LVF implemented as described above in relation to FIG. 4, to provide further laterally varying energy distribution or can be any other appropriate transmission structure with a suitable energy output function, so that incident light on photosensing component 412 similarly has a desired laterally varying photon energy distribution, possibly different than the distribution that would be provided without an additional transmission structure. But this approach runs the risk of losing some of the detailed information in the output light from the optical cavity, so that there is merit in producing a structure as shown in FIGS. 13 and 14 which does not include an additional LVF or other transmission structure.

A detector or other device or apparatus including both an inhomogeneous optical cavity and a photosensing component 412 could be implemented in a wide variety of ways. For example, photosensing component 412 could have a photosensitive surface with an appropriate pixel- or cell-density and the optical cavity could be included in a coating over the photosensitive surface that operates as an LVF.

Photosensing component 412 could be a photosensing array implemented with any appropriate readout technique, such as CMOS or CCD readout, for which cell dimensions of 5-50 μm are currently typical, and smaller cell dimensions are foreseeable. Although it could be a one-dimensional array with a line of cells parallel to the flow direction of arrows 440, implementation with a two-dimensional array could beneficially provide, at each position along the path of object 442, a set of two or more cells in a line perpendicular to the flow direction, with all the cells in the set concurrently photosensing incident light in the same photon energy subrange; sensing results from each set of cells could be used to average or otherwise combine and improve information obtained for a given transmission mode's output light.

Entry and exit light-reflective components 432 and 444 operate as two nonparallel mirrors, with channel 434 being a light-transmission region between them, providing an inhomogeneous optical cavity as described above. With appropriate parameters, the cavity can operate as a Fabry-Perot interferometer, and its transmission properties will be determined by the mirrors and the region between them: The mirrors affect FWHM of peaks of the cavity's transmission spectrum and the reflectivity as well as the width of the stop-band. Also, the refractive index and distances between components 432 and 444 affect or determine the photon energies that are transmitted as well as at what location a certain narrow band of wavelengths is transmitted by the optical cavity.

Each of components 432 and 444 can be implemented as a layered structure with alternating dielectric layers or with metal, deposited in either case on entry glass 402 and exit glass 446. Rather than glasses 402 and 446, the enclosing walls of channel 434 through which light enters and exits could instead be implemented with any other suitable light-transmissive components with inward-facing surfaces that are or can be made reflective, such as by fabrication of appropriate structures on them.

In an illustrative implementation, light source 410 illuminates the optical cavity with broadband illumination. This technique can be used if the cavity is sufficiently thin that only one narrow subrange is transmitted at any particular location.

In other implementations, light source 410 could include or be replaced by an array of narrow band light sources. For example, a single broadband light source like an LED or SLD could be replaced by an array of laser diodes (not shown), all illuminating the entire cavity or each emitting at a respective wavelength to a location of the cavity that transmits its wavelength; since different positions of the optical cavity transmit provide different photon energy subranges, each laser diode in the array could beneficially be positioned or oriented to illuminate a respective position at which the optical cavity transmits the diode's emission wavelength. Alternatively, narrow band light sources could illuminate the entire entry surface of the cavity in sequence.

In general, the output light from the optical cavity can include a discrete transmission mode if the dimensions and refractive index of the optical cavity are appropriate. The presence of object 442, however, can change the refractive index and absorption of the optical cavity due to optical characteristics of object 442. For example, if object 442 has a certain absorption spectrum, it can affect the intensity amplitude Imax and the FWHM (or other intermediate intensity width) of a transmitted mode as illustrated in FIG. 3 and also its contrast as described above; similarly, the refractive index of object 442 can affect photon energies of the mode as illustrated in FIG. 3. These are examples of "encoding information" about optical characteristics, an expression used herein to refer to any operation or combination of operations by which an optical cavity's output light is modified in a way that depends on optical characteristics, such as of object 442. Further description of encoding techniques is provided in co-pending U.S. patent application Ser. No. 11/702,363, entitled "Encoding Optical Cavity Output Light" and incorporated herein by reference in its entirety.

In response to output light from the optical cavity, photosensing component 412 can accordingly obtain sensing results that indicate changes in the central energy, intensity amplitude, contrast, and FWHM of each transmitted mode, providing information about object 442 and its effect on the refractive index and absorption in the optical cavity. The sensing results can then be used, such as by CPU 240 in executing analyte information routine 274 to "obtain information", an expression used herein to refer to any operation or combination of operations performed on sensing results from photosensing an optical cavity's output light and that produce indications of information encoded in the output light; the indications could, for example, be electrical signals, data stored by an appropriate memory device, displayed information, and so forth. Further description of information obtaining techniques is provided in co-pending U.S. patent application Ser. No. 11/702,249, entitled "Obtaining Information From Optical Cavity Output Light" and incorporated herein by reference in its entirety.

Figure 15:
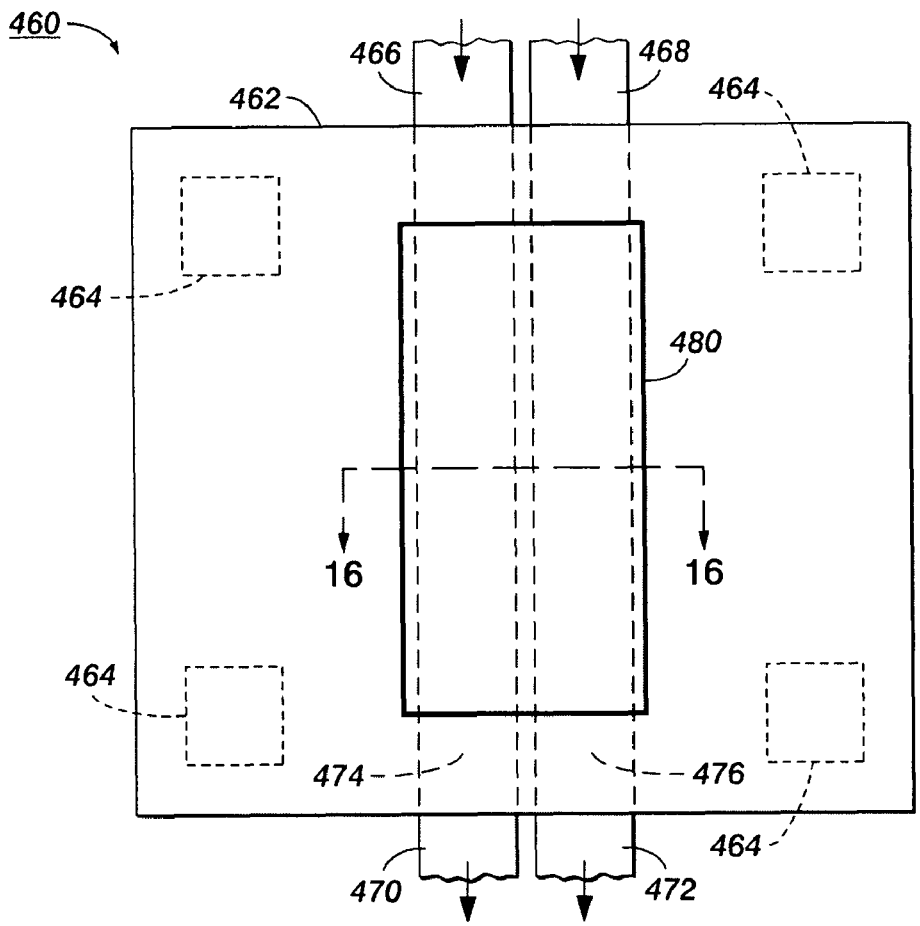
FIG. 15 is a schematic top view of another a implementation of a device as in FIGS. 10 and 11.

FIG. 15 shows device 460, similar to device 400 in FIGS. 13-14 in many ways, and which could similarly be used in an implementation of system 200 in FIGS. 7 and 8. Entry glass 462 (or a slide-like part of any suitable material) and an exit glass (not shown) are of substantially the same size and shape, and their inward-facing surfaces have coatings or other structures that function as light-reflective components, reflecting light into a light-transmissive region between them to operate as an optical cavity. The two glasses are illustratively separated by spacers 464 and the light-transmissive region may also contain fluidic walls or other structures (not shown) that bound two ducts or channels that extend between analyte inlet 466 and reference inlet 468 at one end and analyte outlet 470 and reference outlet 472 on the other end, respectively; as a result, an analyte or a fluid carrying an analyte can enter the optical cavity from inlet 466, can be carried along a path through the optical cavity through analyte channel 474, and can then exit from the optical cavity to outlet 470, while reference fluid can similarly enter from inlet 468, flow through reference channel 476, and exit to outlet 472. A cross section of either channel could have features as illustrated in FIG. 14, except reference channel 476 would not contain object 442.

Figure 16:
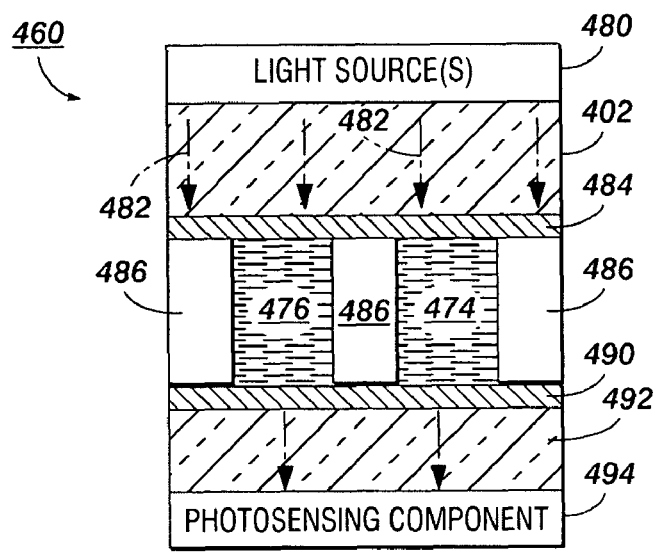
FIG. 16 is a schematic cross section of the device of FIG. 15, taken along the line 16-16.

FIG. 16 shows a transverse cross-section of device 460, viewed along the line 16-16 in FIG. 15. Over or on entry glass 462 is light source component 480, which can include one or more light sources such as lasers, LEDs, or super luminescence diode (SLDs) to illuminate the optical cavity; appropriate optics, such as for beam shaping or diffusers, can be positioned between the light sources and the optical cavity to permit application of a homogeneous light distribution. In the illustrated cross-section, light source component 480 is providing light, represented by arrows 482, which passes through entry glass 462 and through entry light-reflective component 484 before entering channels 474 and 476, which are bounded and separated by wall-like structures 486 as well as light-reflective components 484 and 490. As a result of optical cavity operation, output light is provided through exit glass 492 to photosensing component 494.

Device 460 could be used in a variety of ways. FIGS. 17-21 illustrate some of the ways it could be used in fluidic sensing applications in which channels 474 and 476 contain fluids such as liquid, gas, or aerosol; reference channel 476 could even include vacuum. Optical characteristics such as one or both of refractive index and absorption can be measured with device 460.

Figure 17:
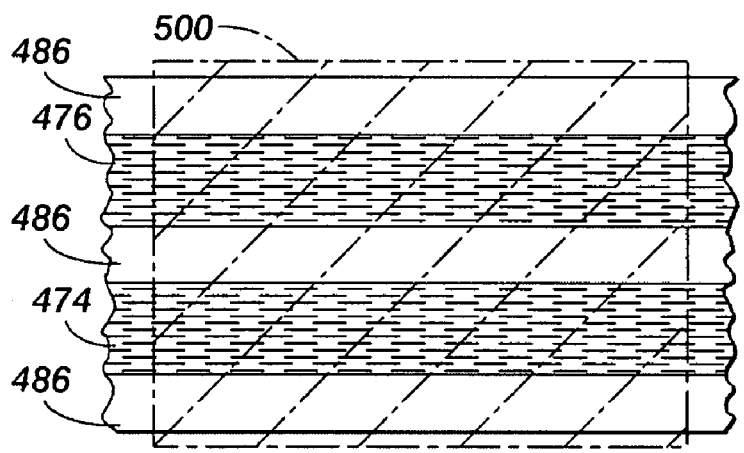
FIG. 17 is a schematic top view of the device of FIGS. 15 and 16, showing a pattern of illumination.

In a first group of implementations, light source component 480 illuminates substantially the entire entry surface of the optical cavity, as shown by illuminated area 500 in FIG. 17. In some examples in this group, light source component 480 provides single narrow band illumination, as would be available, for example, from LEDs, resonant-cavity LEDs, laser diodes including QC lasers, with examples being available over a broad spectral range, from ultraviolet to far infrared. In other examples, component 480 provides multiple narrow band illumination, which could be accomplished, for example, with a combination of several discrete light sources, a resonant cavity LED emitting multiple modes, or a broadband light source modulated with a homogeneous etalon. In these implementations, device 460 can be viewed as an integrated measuring unit for both refractive index and for a set of one or more absorption values, allowing very precise detection of very small changes.

Figure 18:
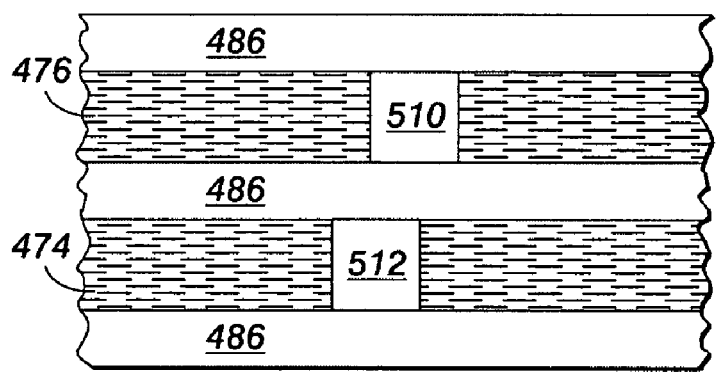
FIG. 18 is a schematic top view of the photosensing component of FIG. 16, showing an example of output light provided in response to illumination as in FIG. 17 with a narrow band of input light.

With single narrow band illumination, a distribution of output light on a photosensitive surface of photosensing component 494 can include one light spot from each of the optical cavities, one from channel 474, and one from channel 476, as shown by light spots 510 and 512 in FIG. 18. Therefore, in this approach, photosensing component 494 can include not only a photosensing array to precisely detect small changes of absorption and refractive index, but alternatively, to get precise absolute values, two PSDs or a quad detector to compare photosensed quantities from analyte channel 474 with those from reference channel 476. Use of PDSs, however, is limited to narrow cavity thicknesses such as $\lambda/2$, $3\lambda/2$, or $5\lambda/2$ in combination with a moderate tilt between the respective surfaces in order to avoid transmission of multiple modes, since a PSD generally requires that light be transmitted only at one position, which depends on factors such as thickness of the optical cavity and the refractive index. One way to achieve this is by properly designing the inhomogeneous cavity, which is desirable to preserve detailed information, as mentioned above. It might also be possible to position an additional band pass filter or linear variable band pass filter (LVF) on top of the PSD's photosensitive area covering a spectral range smaller than the FSR of the optical cavity, in which case the optical cavity should have a large FSR to ensure that light is transmitted to the photosensing component at a single position as in FIG. 18. At the same time, the narrow band light source must have a narrow range comparable to the spectral range covered by the LVF, to avoid creating multiple spots, and this approach is also problematic because of the possible need to decouple the filter from the sensing cavity.

If the above constraints are met, the position of each small single light spot 510 and 512 provides information about refractive index, while intensity provides information about absorption in the narrow range of illumination. Using a PSD, for example, a differential current signal $(I1-I2)/(I1+I2)$ would indicate position with high precision, while a sum signal $(I1+I2)$ would indicate intensity. By choosing a certain narrow band of illumination, one can design a sensor that is specific to that band. For example, most gases, such as $SF_6$, $NH_3$, or $CO_2$, show characteristic absorption peaks in a specific spectral range; particularly interesting spectral ranges for gas sensing are the mid-infrared and the long wave infrared.

Obtaining a single, small light spot from each of channels 474 and 476 allows calibration of absolute measurement. For example, correspondences between light spot locations and known refractive indices can be determined. Also, light intensity can be normalized, easing absolute calibration of absorption coefficient measurement.

Figure 19:
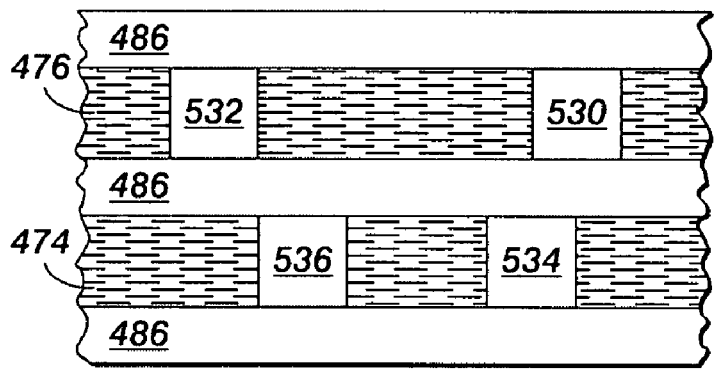
FIG. 19 is another schematic top view of the photosensing component of FIG. 16, showing another example of output light provided in response to illumination as in FIG. 17 with two narrow bands of input light.

In the same setup, device 460 could also be illuminated in sequence by two or more narrow bands, in which case illumination by each narrow band would again provide illuminated area 500 as in FIG. 17, but one narrow band would provide light spots 530 and 534, while the other would provide light spots 532 and 536, as in FIG. 19; as above, spots from both channels 474 and 476 allow calibration of absolute measurement. For example, refractive index and absorption could be measured in succession with different illumination wavelengths, such as two different narrow band light sources switched on and off sequentially, in order to enhance specificity and sensitivity. Strong absorption may influence the result of refractive index measurement and vice versa.

To get more specific information about an analyte, multiple wavelengths can be used sequentially for absorption measurement, which allows determination of absorption values in different absorption ranges where specific absorption is expected. A similar result could be achieved by using a row of measuring units, each designed to capture information from a respective different spectral range, e.g. in the mid-infrared or long wave infrared range.

Finally, the same setup could be used, but with a photosensing array in place of PSDs or a quadsensor. This setup could be operated in the ways described above, but also an array can be used to concurrently photosense multiple light spots with different sets of cells. This is possible if each light source of a light source array produces one light spot. If the optical cavity is sufficiently thin, with thickness $\lambda/2$, several narrow band light sources could alternatively illuminate the entire cavity, transmitting only one wavelength at one position.

A more complex approach using a photosensing array is to illuminate an optical cavity with a narrow band light source as in FIG. 17, where the optical cavity produces multiple light spots from different order Fabry-Perot modes of the narrow band, which could produce concurrent light spots as in FIG. 19. Therefore, one narrow band can be measured at multiple separated light spot positions, increasing signal-to-noise ratio of measurement.

In order to achieve multiple light spots using this multiple-mode approach, the FWHM of the light source and FSR of the optical cavity must be chosen such that the incoming light causes output light from two or more modes, each at a respective different position. As above, position and intensity of each spot provides information on an analyte's refractive index and absorption coefficient. Also, use of analyte channel 474 and reference channel 476 permits calibration for absolute measurement, while calibration to environmental conditions (e.g. temperature) allows for higher precision. The multiple-mode approach can also be extended by using multiple different narrow band light sources in sequence, each of which produces multiple light spots, allowing measurement of refractive index and absorption at different wavelengths.

Figure 20:
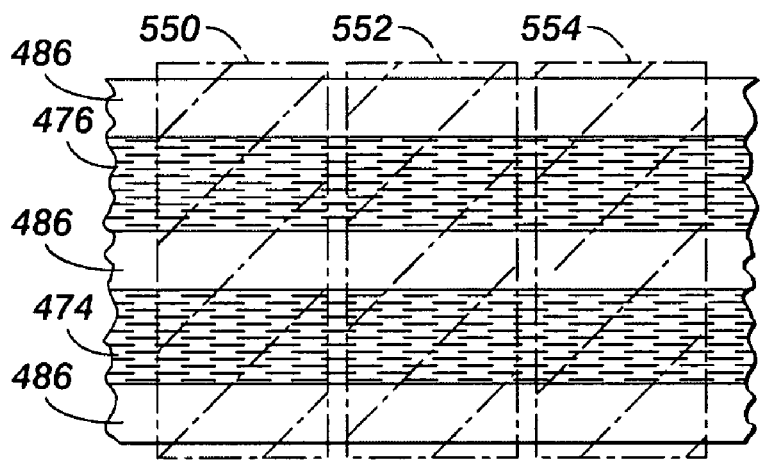
FIG. 20 is another schematic top view of the device of FIGS. 15 and 16, showing another pattern of illumination.

FIG. 20 illustrates a multiple concurrent different narrow band light source approach, in which an array of light sources, illustratively three, provide respective illuminated areas 550, 552, and 554. The optical cavity and the array of light sources are aligned so that each light source illuminates the cavity in a range in which the light source has an appropriate Fabry-Perot mode. Alternatively, a light source with several narrow wavelength bands, produced in any of the ways mentioned above, could illuminate the entire cavity as in FIG. 17 such that each band is transmitting at a different position, which would work only with cavities that have very high FSRs, while the alignment technique would work with smaller FSRs.

Figure 21:
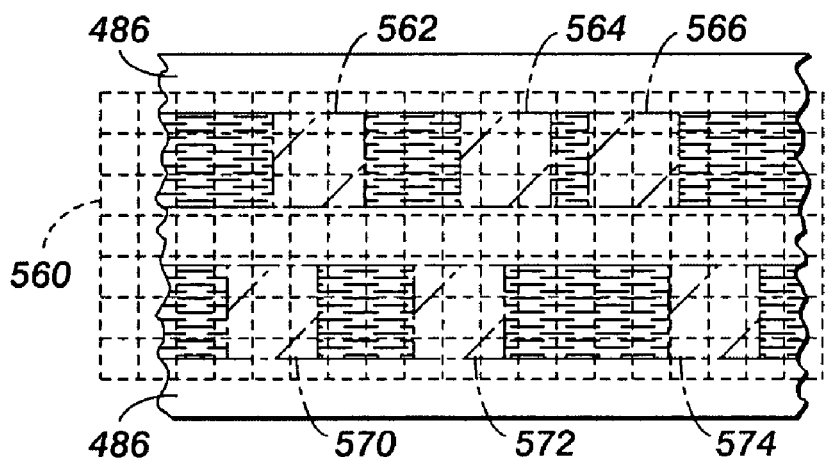
FIG. 21 is a schematic top view of the photosensing component of FIG. 16, showing an example of output light provided in response to illumination as in FIG. 20.

FIG. 21 shows a pattern of light on photosensing array 560 produced with this approach. Light spots 562, 564, and 566 on reference channel 476 are paired respectively with light spots 570, 572, and 574 on analyte channel 474. In other words, illuminated area 550 produces light spots 562 and 570; area 552 produces light spots 564 and 572; and area 554 produces light spots 566 and 574. Positions and intensities of light spots again provide information about refractive index and absorption. Reference channel 474 can be used to calibrate for absolute measurement, as described above.

In a different approach, broadband illumination is provided to illuminated area 500 on an optical cavity as in FIG. 17. If the optical cavity is sufficiently thin, with thickness λ/2, only one wavelength is transmitted at one position. As a result, each cell of a photosensing array receives light in a respective energy subrange, with intensity depending on absorption of the analyte in the subrange. In addition to calibrating for absolute measurement using reference channel 476 and a narrow band light source, an additional line of cells in the array could detect inhomogeneities in the incident light, allowing for reference-cell correction. It might be necessary in some implementations to filter the broadband illumination so that, at a particular spot, only one Fabry-Perot mode is transmitted by the optical cavity; if a cavity with greater optical thickness is used, i.e. 3λ/2 or more, filtering can cut off higher modes, and an LVF might be an appropriate type of filter because the wavelengths that need to be blocked vary laterally.

Various techniques can be used to correct for inhomogeneous illumination of device 460 or other similar devices. As noted above, reference-based adjustment or correction can be used. An easier self-referencing approach with a photosensing array is to determine the FWHM (or other intermediate intensity width) of a transmitted Fabry-Perot mode, contrast, or another value providing a measure of absorption independent of inhomogeneities in illumination; in most cases it is enough to determine a single intensity ratio within the transmitted mode in order to get a value for its spectral width. This self-referencing is especially interesting for a thick graded cavity that is transmitting multiple Fabry-Perot modes of a given wavelength; in this case, cavity-only absorption data can be obtained, as described in U.S. patent application Ser. No. 11/702,249, entitled "Obtaining Information From Optical Cavity Output Light" and incorporated herein by reference in its entirety. But self-referencing is not useful with broadband illumination approaches as described above.

If analyte channel 474 includes homogeneous analyte, photosensed quantities can be used directly to obtain information about refractive index and absorption of the analyte. But if a channel's contents are inhomogeneous, such as due to discrete biological cells or other objects in a fluid, measurements will be a mixture of optical characteristics of the objects and the fluid. In this case, techniques that take into account the size of the cell and its position and motion along a fluidic path can be used, as also described in U.S. patent application Ser. No. 11/702,249, referenced above. Long integration times can be used without losing throughput capacity; step-by-step gathering of absorption values as an object moves along its path can also be helpful. But a graded inhomogeneous cavity as in FIG. 14 will have changing fill factor of the analyte, because the ratio of object volume to channel volume changes; also, the gradient in the channel's diameter will influence flow speed.

Figure 22:
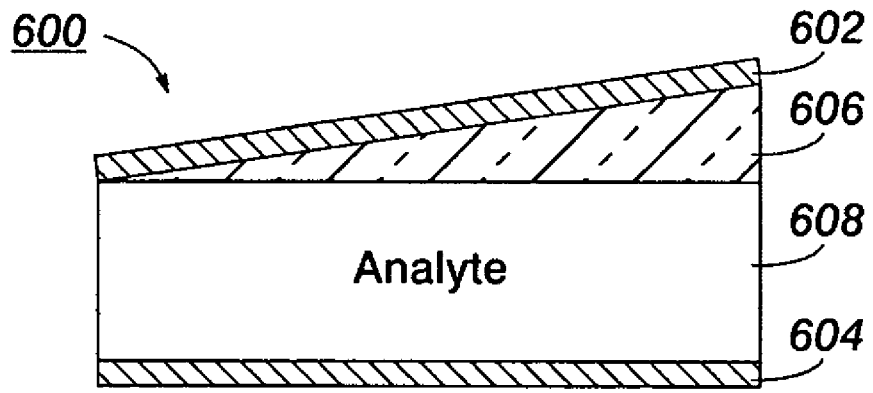
FIG. 22 is a schematic cross section of another inhomogeneous optical cavity with a wedge-like component in its light-transmissive region.

FIG. 22 illustrates an approach that addresses the problem of uneven channel diameter. Device 600 includes light-reflective components 602 and 604. In the light-transmissive region between them, wedged spacer 606 maintains channel cross-sectional area approximately constant. The illustrated technique is a possible solution to challenges that arise due to tilt's effect on flow speed of cells or other analytes through channels. In FIG. 22, channel 608 can be homogeneous, and uniform in cross section, so that the filling factor of the analyte (e.g. cell volume/channel volume) does not change due to tilt of the analyte-containing cavity, which would also influence the cell's flow speed through the channel.

Figure 23:
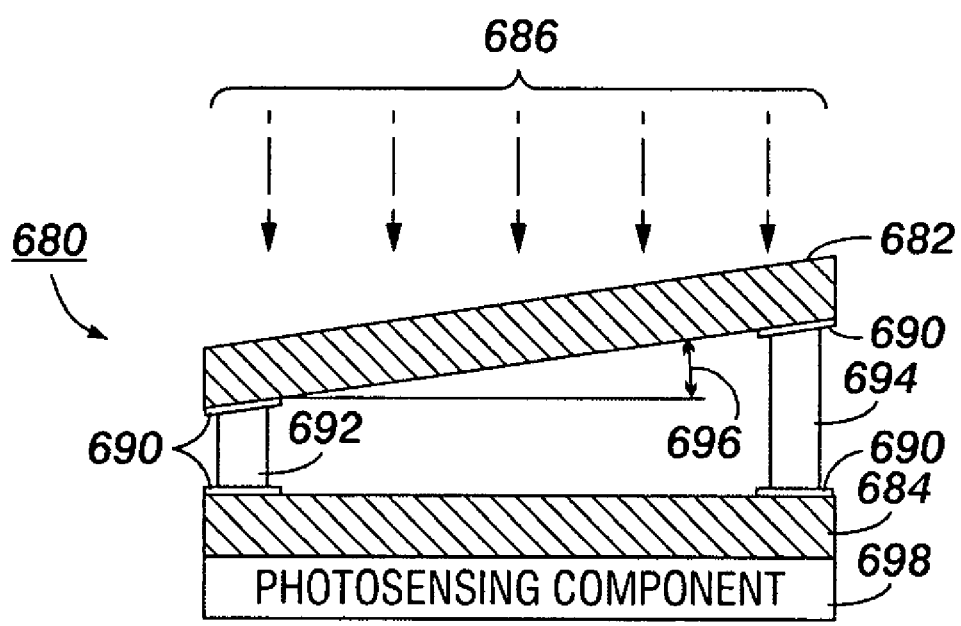
FIG. 23 is a schematic side view of an optical cavity that can be tuned by modifying the length of elastomer spacers and could be used in a system as in FIGS. 7 and 8.

FIG. 23 shows device 680, which can also be used in a system as in FIGS. 7 and 8. Light-reflective components 682 and 684, together with the region between them, can operate as an inhomogeneous optical cavity when illuminated by input light, represented by arrows 686.

Components 682 and 684 have electrodes 690 on their inward surfaces, facing each other and with elastically deformable spacers 692 and 694 between them. As a result, signals can be provided to electrodes 690 to cause changes in distances between the inward, reflective surfaces of components 682 and 684, such as electrostatically, electromagnetically, or piezoelectrically, changing the shape of the region between them, as suggested by angle 696. The distance between electrodes and the angle of tilt can be very precisely measured and controlled, such as by capacitive measurement, allowing adjustment of device 680 for a particular application and also allowing use of lock-in techniques.

At positions where photon energy of input light is the same as a transmission mode of device 680, light is transmitted to photosensing component 698, which obtains sensing results. If analyte is present in the region between structures 682 and 684, optical cavity operation can provide analyte-affected output light, implementing features described above in relation to FIG. 10.

Some of the implementations described above in relation to FIGS. 1-23 illustrate examples of devices that include a photosensing component and an optical cavity structure. The photosensing component has one or more photosensitive surfaces. The optical cavity structure includes an inhomogeneous transmissive optical cavity with a light-transmissive region between two inward reflection surfaces, and also includes an analyte region that can contain analyte within the light-transmissive region; presence of the analyte affects the optical cavity's output light. The photosensing component is positioned to receive the output light and, in response, provides sensing results that include information about the analyte's optical characteristics.

In specific implementations, the photosensing component can include one photosensitive surface that receives the optical cavity's output light with no intervening optical component. The optical cavity structure can also include two light-reflective components, each of which includes one of the reflection surfaces.

Some of the implementations described above in relation to FIGS. 1-23 also illustrate examples of a system that includes an optical cavity device and an optical cavity structure as described above, connected to each other. The system also includes monitor circuitry connected to receive the sensing results from the photosensing component, and the monitor circuitry uses the sensing results to monitor the analyte's optical characteristics.

In specific implementations, the system can also include a light source component. The light source component can include a broadband light source that provides input light to the optical cavity in a broad photon energy band. Or, the light source can include an array with multiple narrow band light sources, each providing input light in a respective narrow photon energy band; the respective photon energy bands are different.

Some of the implementations in FIGS. 1-23 illustrate examples of a method that includes illuminating an optical cavity structure and using a photosensing component connected to the optical cavity structure to photosense the output light. The optical cavity structure includes a transmissive optical cavity with a light-transmissive region between first and second inward reflection surfaces. The light-transmissive region includes an analyte region in which analyte can be present. In response to illumination with analyte in the analyte region, the optical cavity provides output light with a laterally varying output energy distribution that includes information about an optical characteristic of the analyte. The photosensing component provides sensing results indicating the optical characteristic.

In specific implementations, the method can include positioning analyte in the analyte region. The analyte region can be inside a channel, and analyte can be positioned by being carried on a fluid through the channel.

In further specific implementations, the optical cavity can be inhomogeneous. The illumination can be uniform across a surface of the optical cavity structure; for example, the cavity can be sufficiently thin to transmit only a single mode at each position, and it can be illuminated with broadband illumination or it can be illuminated in a set of narrow photon energy bands. The optical cavity can be a linearly variable filter. Also, an inhomogeneous optical cavity could be illuminated in sequence with different narrow photon energy bands or each of a set of regions could be illuminated in a respective narrow photon energy band.

In further specific implementations, the optical cavity could be homogeneous, with illumination incident on a surface across a range of angles of incidence. The photosensing component could be a photosensing array and photosensed quantities could be read out from its cells. Or the photosensing component could be a position-sensitive detector, and signals could indicate a light spot's position on the detector.

Some of the implementations described above in relation to FIGS. 1-23 are examples of a method of producing an optical cavity device that includes a photosensing component and a connected optical cavity structure as described above. The optical cavity structure is produced so that it includes an analyte region that can contain analyte within the light-transmissive region of an inhomogeneous transmissive optical cavity. Presence of the analyte affects the optical cavity's output light. In response to the analyte-affected output light, the photosensing component provides sensing results that includes information about the analyte's optical characteristics.

In a specific implementation, the optical cavity structure is produced on one or more of the photosensitive surfaces of the photosensing component.

Some of the implementations described above in relation to FIGS. 1-23 are examples of a device that includes a photosensing component as described above and an optical cavity structure, with the photosensing component and the optical cavity structure being connected. The optical cavity structure includes an optical cavity with an analyte region that can contain analytes. With analyte present, the optical cavity has, in response to input light from external light sources, an analyte-affected laterally varying energy output function. The optical cavity structure also includes a light interface surface at which the optical cavity can provide output light to the photosensitive surfaces in response to the input light. As a result of the analyte-affected energy output function, the optical cavity providing analyte-affected output light with a laterally varying intensity distribution on the photosensitive surfaces. In response, the photosensing component provides sensing results that include information about the analyte's optical characteristics.

In specific implementations, the information can include information about at least one of refractive index, absorption coefficient, and absorption spectrum of the analyte. The photosensing component can include at least one of a photosensor array and a position-sensitive detector. The photosensing component can include only one photosensitive surface, and the optical cavity structure can be a layered structure with a lowest layer deposited on the photosensitive surface; the photosensing component and the optical cavity structure can be connected by an interface between the lowest layer and the photosensitive surface.

In further specific implementations, the photosensing component and the optical cavity structure can be connected by a support structure that supports them both; the device can also include an optical component on the support structure, receiving at least part of the analyte-affected output light and, in response, providing the analyte-affected, laterally varying intensity distribution on the photosensitive surfaces. The optical component can be a lens that images the analyte-affected output light onto the photosensitive surfaces.

In further specific implementations, the optical cavity structure can have lateral inhomogeneity that causes the laterally varying energy output function. For example, the lateral inhomogeneity can be a linear gradient of optical thickness.

In further specific implementations, the device can also include external light sources. The external light sources can include two or more light sources, each providing light within a respective photon energy subrange, with at least two of the respective subranges being different from each other. The external light sources can include an array of light sources on the optical cavity structure.

In further specific implementations, the external light sources can provide input light within a range of photon energies, and the analyte-affected intensity distribution can result from the input light's range and the optical cavity structure's characteristics. For example, the input light's range can be a narrow band and the optical cavity structure can have a free spectral range such that the analyte-affected intensity distribution includes only one light spot. Or the input light's range can be narrow band and the optical cavity structure can have free spectral range such that the analyte-affected intensity distribution includes two or more light spots; each light spot could result from a respective Fabry-Perot mode of the optical cavity. Or the input light's range could be a broad band with discreet subranges and the optical cavity structure's analyte-affected energy output function could provide output light for each subrange from a respective position on the exit surface; the positions of the subranges could all be distinguishable from each other in the analyte-affected intensity distribution.

In further specific implementations, the optical cavity structure can be a transmission structure that has an entry surface through which it receives light from external light sources. The analyte-affected energy output function could be a laterally varying energy transmission function between the entry surface and the exit surface. The optical cavity could also include a reference region that contains a reference medium; for example, the analyte region could be a first channel through which analyte can be carried by flowing medium, and the reference region could be a second channel through which medium without analyte could flow, with the two channels being parallel within the optical cavity structure. The photosensing component can also include an array with two parallel lines of cells, with a first line receiving the analyte-affected intensity distribution, and with the second line receiving an intensity distribution of light from the external light sources, resulting from light that has not passed through the optical cavity structure.

Some of the implementations described above in relation to FIGS. 1-23 are examples of systems that include the same components as the devices described above, and also include monitor circuitry connected to receive sensing results from the photosensing component, which it uses to monitor the analyte's optical characteristics.

In specific implementations, the monitor circuitry can use the sensing results to obtain information about at least one of refractive index, absorption coefficient, and absorption-energy function of the analyte. The monitor circuitry can use the sensing results to obtain a differential quantity. If the photosensing component includes an array, the monitor circuitry can receive sensing results from two sets of cells that receive two parts of the analyte-affected output light; for example, the sets of cells could be in separated positions of the array, and two different light sources could provide the two parts of the analyte-affected output light, respectively. Or, the two parts of the analyte-affected output light could be within respective subranges that are different, and are provided by two different light sources; the analyte-affected energy output function could provide each subrange's output light from a respective position, and the positions could be distinguishable from each other in the analyte-affected intensity distribution.

Some of the implementations described above in relation to FIGS. 1-23 are examples of a method that includes providing input light from one or more external light sources to an optical cavity structure. The optical cavity structure includes an optical cavity with an analyte region that can contain analyte; with analyte present, the optical cavity has, in response to the input light, an analyte-affected laterally varying energy output function as a result of the analyte's optical characteristics. The optical cavity structure also has an exit surface through which the optical cavity provides output light; with the analyte present, the optical cavity provides analyte-affected output light through the exit surface. The method receives the analyte-affected output light on one or more photosensitive surfaces of a photosensing component, with a laterally varying intensity distribution as a result of the energy output function. In response, the photosensing component provides sensing results, and the method uses the sensing results to monitor the analyte's optical characteristics.

In specific implementations, the external light sources can include two or more light sources with respective photon energy subranges, and the method can operate the light sources in sequence so that each light source provides light within its subrange during a respective part of the sequence. The optical cavity structure can include a graded cavity etalon that includes the analyte region, and the method can position the analyte in the analyte region. Positioning the analyte can include fluidically carrying the analyte into the analyte region using at least one of a gas, an aerosol, and a liquid.

The implementations in FIGS. 1-23 illustrate various applications of techniques as described above, including photosensing output light from modes of optical cavities that contain analyte and obtaining information about the analyte, such as about its refractive index and absorption coefficient. The techniques could be readily extended to obtain information about polarization and fluorescence.

Techniques that obtain information about analytes, as exemplified by the implementations in FIGS. 1-23, can be applied in many measuring techniques. For example, fluidic sensing, e.g. liquid, gas, or aerosol, could be performed with infrared illumination. For these applications, an optical cavity with features similar to commercially available LVFs in the visible range might be appropriate. Especially interesting spectral ranges for gas sensing include 8 µm to 14 µm with 600 nm/mm gradient, and with the mirror spaced at 12-20 µm over 1 cm for a $3\lambda/2$ cavity and 3 µm to 5 µm with 200 nm/mm gradient, and with the mirror spaced at 4.5-7.5 µm over 1 cm for a $3\lambda/2$ cavity. Other interesting ranges for sensing applications include the mid-infrared (2-5 µm) and long wave infrared (6-12 µm).

Another potential area of application is in distinguishing objects such as biological cells, such as by counting, sorting, and so forth. Using a reference medium with no cells or objects in a device as in FIG. 15 can eliminate the influence of varying environmental changes. Related techniques could be used to obtain probability of a certain type of object, such as cancerous cells. Also, for rare cell scanning, the above techniques may be useful because they can provide high throughput (counting/sorting speed): if a high number of parallel channels can be used, e.g. 200, it may be possible to sort 1 out of 10,000,000 cells within a few seconds using a device with the typical dimensions of a CMOS detector chip. Techniques for distinguishing objects are described in greater detail in co-pending U.S. patent application Ser. No. 11/702,328, entitled "Distinguishing Objects" and incorporated herein by reference in its entirety.

Another potential area of application is in implantable products useful to obtain information about analytes such as glucose in bodily fluids, as described in co-pending U.S. patent application Ser. No. 11/702,329, entitled "Implanting Optical Cavity Structures" and incorporated herein by reference in its entirety. Since typical dimensions for the cavity thickness of a device as described are in the 3-12 µm range, such devices should be able to handle high water background absorption in the 3 µm as well as the 8-12 µm range.

Various of the techniques described above have been successfully implemented or simulated, including the production and operation of chip-size detectors. The influence of an analyte in the cavity of an etalon has been experimentally tested and simulated.

The exemplary implementations described above allow compact, inexpensive components to rapidly and accurately perform operations such as measuring optical characteristics of fluids, biological cells, glucose, and other analytes.

The exemplary implementations described above employ optical cavities with specific parameters and modes, but a wide variety of cavities could be used. Cavities with widths in the range from a few µm to hundreds of µm are feasible, and photon energies ranging from the ultraviolet up to the far infrared could be sampled.

In addition, components could have various shapes, dimensions, or other numerical or qualitative characteristics other than those illustrated and described above. For example, in some exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing an optical cavity and the cell sensing area; for example, the width may be as small as 0.1 nm or as great as tens of nanometers.

Some of the above exemplary implementations involve specific materials, such as in photosensor arrays or position-sensitive detectors and optical cavities, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information whether based on CCD, CMOS, or other techniques. Various commercially available detector arrays have pixel densities as high as ten megapixels, and some high density ICs have become relatively inexpensive.

Similarly, optical cavities could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in optical cavities may vary from 30 nm up to a few hundred nanometers.

Some of the above exemplary implementations could involve particular types of optical cavity structures, such as Bragg mirrors and paired distributed Bragg reflectors separated by a Fabry-Perot cavity, but, more generally, any appropriate optical cavity structure could be used to produce a laterally varying energy distribution, including a homogeneous optical cavity illuminated across a range of angles of incidence by a point light source. Various techniques could be used to produce optical cavities structures with laterally varying optical thickness in addition to those described above, including, during deposition, tilting the substrate, using a shadow mask, or using a temperature gradient to obtain graded layer thickness; also, during homogeneous deposition, off-axis doping, such as by e-beam, MBE, or MOVPE, could produce lateral variation.

Some of the above exemplary implementations use specific lasers or other light sources to obtain light with desired characteristics, but various other light source techniques could be used within the scope of the invention. Various propagation components that propagate light between other components could also be employed.

The exemplary implementation in FIGS. 8 and 9 employs a CPU, which could be a microprocessor or any other appropriate component. Furthermore, as noted above, adjustment, combining, and other operations on photosensed quantities could be done either digitally or with analog signals, and could be done either on the same IC as a photosensor array, on other components, or on a combination of the two, with any appropriate combination of software or hardware.

The above exemplary implementations generally involve production and/or use of ICs and other photosensing components, optical cavities, light sources, transmission structures, monitor circuitry, processing circuitry, and control circuitry following particular operations, but different operations could be performed, the order of the operations could be modified, and additional operations could be added within the scope of the invention. For example, readout of adjusted or unadjusted photosensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:
1. A device comprising:
a photosensing component with one or more photosensitive surfaces; and
an optical cavity structure including:
an inhomogeneous transmissive optical cavity with a light-transmissive region between first and second inward reflection surfaces; and
an analyte region that can contain analyte within the light-transmissive region, presence of the analyte in the analyte region affecting the optical cavity's output light; the photosensing component being positioned to receive the output light and, in response, the photosensing component providing sensing results that include information about the analyte's optical characteristics, and wherein the photosensing component is further positioned so that received analyte-affected output light has laterally varying wavelength dependent photon energy distribution on the photosensitive surfaces; the photosensing component providing the sensing results indicating the laterally varying wavelength dependent photon energy distribution.

2. A system comprising:
an optical cavity device that includes:
a photosensing component with one or more photosensitive surfaces; and
connected to the photosensing component, an optical cavity structure that includes:
an inhomogeneous optical cavity with a light-transmissive region between first and second inward reflection surfaces; and
an analyte region that can contain analyte within the light-transmissive region, presence of the analyte in the analyte region affecting the optical cavity's output light; in response to analyte-affected output light from the optical cavity, the photosensing component providing sensing results that include information about the analyte's optical characteristics; and
monitor circuitry connected to receive the sensing results from the photosensing component, the monitor circuitry using the sensing results to monitor the analyte's optical characteristics, and wherein the photosensing component is further positioned so that received analyte-affected output light has laterally varying wavelength dependent photon energy distribution on the photosensitive surfaces; the photosensing component providing the sensing results indicating the laterally varying wavelength dependent photon energy distribution.

3. The system of claim 2, further comprising:
a light source component that includes at least one of:
a broadband light source that provides input light to the optical cavity in a broad photon energy band; and
an array with multiple narrow band light sources, each providing input light to the optical cavity in a respective narrow photon energy band, the respective photon energy bands of at least two of the narrow band light sources being different.

4. A method comprising:
illuminating an optical cavity structure that includes a transmissive inhomogeneous optical cavity with a light-transmissive region between first and second inward reflection surfaces, the light-transmissive region including an analyte region in which analyte can be present; in response to illumination with analyte in the analyte region, the optical cavity providing output light with a laterally varying wavelength dependent output energy distribution that includes information about an optical characteristic of the analyte; and
using a photosensing component connected to the optical cavity structure to photosense the output light, the photosensing component providing sensing results indicating the laterally varying wavelength dependent output energy distribution that conveys information about the-optical characteristic of the analyte.

5. The method of claim 4 in which the illumination is uniform across a surface of the optical cavity structure.

6. The method of claim 5 in which the inhomogeneous optical cavity has an exit surface that includes positions, the inhomogeneous optical cavity being sufficiently thin to transmit only a single mode at each position, the act of illuminating the optical cavity structure comprising one of:
  illuminating the inhomogeneous optical cavity with broadband illumination; and
  illuminating the inhomogeneous optical cavity in a set of narrow photon energy bands.

7. The method of claim 5 in which the optical cavity is a linearly variable filter, linearly varying orthogonally to a plane of one of the reflection surfaces.

8. The method of claim 4 in which the act of illuminating the optical cavity structure comprises one of:
  illuminating the inhomogeneous optical cavity in a sequence of illuminations, each illumination being in a respective narrow photon energy band, at least two of the photon energy bands being different from each other; and
  illuminating a set of regions of the inhomogeneous optical cavity, each region being illuminated in a respective narrow photon energy band.

9. The method of claim 4 in which, in response to illumination with analyte in the analyte region, the optical cavity has an analyte affected laterally varying wavelength dependent energy output function and, as a result, photosensitive surfaces in the photosensing component receive the laterally varying wavelength dependent output energy distribution.

10. A method comprising:
  illuminating an optical cavity structure that includes an optical cavity with a light-transmissive region between first and second inward reflection surfaces, the light-transmissive region including an analyte region in which analyte can be present;
  in response to illumination with analyte in the analyte region, the optical cavity providing output light with a laterally varying wavelength dependent output energy distribution that includes information about an optical characteristic of the analyte; and
  using a photosensing component connected to the optical cavity structure to photo sense the output light, the photosensing component providing sensing results indicating the laterally varying wavelength dependent output energy distribution that conveys information about the optical characteristic of the analyte;
  the act of illuminating the optical cavity structure comprising at least one of:
  illuminating uniformly across a surface of the optical cavity structure; the optical cavity being inhomogeneous;
  illuminating the optical cavity structure with broadband illumination; the optical cavity being inhomogeneous;
  illuminating the optical cavity structure in a set of narrow photon energy bands; the optical cavity being inhomogeneous;
  illuminating the optical cavity structure in a sequence of illuminations, each illumination being in a respective narrow photon energy band, at least two of the photon energy bands being different from each other; the optical cavity being inhomogeneous;
  illuminating a set of regions of the optical cavity structure, each region being illuminated in a respective narrow photon energy band; the optical cavity being inhomogeneous; and
  illuminating a surface of the optical cavity structure across a range of angles of incidence; the optical cavity being homogeneous.

11. A device comprising:
  a photosensing component with one or more photosensitive surfaces and a set of positions in the photosensitive surfaces; and
  an optical cavity structure including:
  first and second inward reflection surfaces and, between them, a light transmissive region, the light-transmissive region having laterally varying optical thickness; and
  an analyte region capable of containing analyte within the light-transmissive region;
  the optical cavity structure being structured so that:
  due to the laterally varying optical thickness, the light-transmissive region and the first and second inward reflection surfaces are operable as an inhomogeneous optical cavity with analyte not present in the analyte region and also with analyte present in the analyte region; the optical cavity providing output light through an exit surface in a set of one or more transmission modes;
  with an analyte not present in the analyte region, the optical cavity providing output light in which each of the set of modes has a respective first intensity-position function; and
  with the analyte present in the analyte region, the optical cavity providing output light in which each of the set of modes has a respective second intensity position function; at least one mode's first and second intensity-position functions being different, the difference indicating information about an optical characteristic of the analyte, the optical characteristic including at least one of refractive index, absorption coefficient, and absorption spectrum;
  the light-transmissive region's optical thickness having one of:
  lateral variation sufficiently small that the set of modes includes only a single mode; and
  lateral variation sufficiently small that intensity-position functions of adjacent modes do not interfere with each other;
  the photosensing component being positioned to receive the output light from the exit surface and so that, as a result of the light-transmissive region's laterally varying optical thickness, output light incident on the set of positions has laterally varying wavelength dependent photon energy distribution; in response to the laterally varying wavelength dependent photon energy distribution, the photosensing component providing sensing results indicating the laterally varying wavelength dependent photon energy distribution, wherein the laterally varying wavelength dependent photon energy distribution conveys the information about the analyte's optical characteristic.

12. The device in claim 11 which the photosensing component includes one photosensitive surface that receives the optical cavity's output light with no intervening optical component.

13. The device of claim 11 in which the optical cavity structure further includes: first and second light-reflective components that include the first and second reflection surfaces, respectively.

14. The method of claim 10 in which, in response to illumination with analyte in the analyte region, the optical cavity has an analyte affected laterally varying wavelength dependent energy output function and, as a result, photosensitive surfaces in the photosensing component receive the laterally varying wavelength dependent output energy distribution.

15. The method of claim 10, further comprising:
  positioning analyte in the analyte region.

16. The method of claim 15 in which the analyte region is inside a channel, the act of positioning analyte comprising:
  carrying the analyte on a fluid through the channel.

17. The method of claim 10 in which the photosensing component is a photosensing array, the act of using the photosensing component comprising:
  reading out photosensed quantities from cells of the photosensing array.

18. The method of claim 10 in which the photosensing component is a position-sensitive detector and the laterally varying output energy distribution includes a light spot, the act of using the photosensing component comprising:
  providing signals indicating the light spot's position on the position-sensitive detector.

19. A method comprising:
  illuminating an optical cavity structure that includes a homogeneous transmissive optical cavity with a light-transmissive region between first and second inward reflection surfaces, the light-transmissive region including an analyte region in which analyte can be present; in response to illumination with analyte in the analyte region, the illumination being incident on a surface of the optical cavity structure across a range of angles of incidence, the optical cavity providing output light with a laterally varying output energy distribution that includes information about an optical characteristic of the analyte; and
  using a photosensing component connected to the optical cavity structure to photosense the output light, the photosensing component providing sensing results indicating the optical characteristic of the analyte.

20. A device comprising:
  a photosensing component with one or more photosensitive surfaces; and
  an optical cavity structure that can receive input light from external light sources;
  the photosensing component and the optical cavity structure being connected;
  the optical cavity structure including:
    an optical cavity with an analyte region that can contain analyte; with analyte present in the analyte region, the optical cavity having, in response to input light from one or more external light sources, an analyte-affected laterally varying energy output function; and
    a light interface surface at which the optical cavity can provide output light to the photosensitive surfaces in response to the input light; with the analyte present in the analyte region, the optical cavity providing analyte-affected output light at the light interface surface in response to the input light; as a result of the analyte-affected energy output function, the analyte-affected output light providing an analyte-affected, laterally varying intensity distribution on the photosensitive surfaces;
  in response to the analyte-affected output light, the photosensing component providing sensing results that include information about the analyte's optical characteristics.

21. The device of claim 20 in which the information about the analyte's optical characteristics includes information about at least one of refractive index, absorption coefficient, and absorption spectrum of the analyte.

22. The device of claim 20 in which the photosensing component includes at least one of a photosensor array and a position-sensitive detector.

23. The device of claim 20 in which the photosensing component includes only one photosensitive surface, the optical cavity structure being a layered structure with a lowest layer deposited on the one photosensitive surface; the photosensing component and the optical cavity structure being connected by an interface between the lowest layer and the photosensitive surface.

24. The device of claim 20 in which the photosensing component and the optical cavity structure are connected by a support structure that supports them both; the device further comprising:
  an optical component supported on the support structure; the optical component receiving at least part of the analyte-affected output light from the light interface surface and, in response, providing the analyte-affected, laterally varying intensity distribution on the photosensitive surfaces.

25. The device of claim 24 in which the optical component is a lens that images the analyte-affected output light onto the photosensitive surfaces.

26. The device of claim 20 in which the optical cavity structure has lateral inhomogeneity, the lateral inhomogeneity causing the laterally varying energy output function.

* * * * *